(12) United States Patent
Hinnebusch

(10) Patent No.: US 8,103,517 B2
(45) Date of Patent: Jan. 24, 2012

(54) SYSTEM AND METHOD TO IMPROVE FITNESS TRAINING

(76) Inventor: Michael Hinnebusch, El Paso, TX (US)

( * ) Notice: Subject to any disclaimer, the term of this patent is extended or adjusted under 35 U.S.C. 154(b) by 1427 days.

(21) Appl. No.: 10/015,866

(22) Filed: Dec. 12, 2001

(65) Prior Publication Data

US 2002/0055419 A1 May 9, 2002

Related U.S. Application Data

(63) Continuation-in-part of application No. 09/977,557, filed on Oct. 15, 2001, now abandoned, which is a continuation-in-part of application No. 09/829,757, filed on Apr. 10, 2001, now abandoned.

(60) Provisional application No. 60/196,498, filed on Apr. 12, 2000.

(51) Int. Cl.
*G06Q 99/00* (2006.01)
*A63B 21/00* (2006.01)

(52) U.S. Cl. .............. 705/1.1; 702/182; 482/4; 482/8; 482/9; 705/51

(58) Field of Classification Search ............. 705/14, 705/2, 1, 1.1, 14.68; 713/201; 709/224; 395/200.5; 482/54, 1–9, 57
See application file for complete search history.

(56) References Cited

U.S. PATENT DOCUMENTS

| | | | | |
|---|---|---|---|---|
| 4,817,940 A | * | 4/1989 | Shaw et al. | 482/9 |
| 5,502,806 A | * | 3/1996 | Mahoney et al. | 715/839 |
| 5,690,582 A | * | 11/1997 | Ulrich et al. | 482/4 |
| 5,702,323 A | | 12/1997 | Poulton | 482/8 |
| 5,720,619 A | | 2/1998 | Fisslinger | 434/336 |
| 5,836,770 A | * | 11/1998 | Powers | 434/247 |
| 5,904,484 A | | 5/1999 | Burns | 434/252 |

(Continued)

FOREIGN PATENT DOCUMENTS

EP 623367 A1 * 11/1994

OTHER PUBLICATIONS http://web.archive.org/web/199908280911333/http://www.sfgate.com/cgi-bin/article.cgi?file=/chronicle/archive/1988/05/05/BU102799.DTL&type=printable.*

(Continued)

*Primary Examiner* — John Hayes
*Assistant Examiner* — Freda A Nelson
(74) *Attorney, Agent, or Firm* — Peter K. Trzyna, Esq.

(57) ABSTRACT

A method for creating a personalized exercise routine with at least one user interface used in connection with forming machine-readable instructions protected as private to a user subsequently carrying out the exercise routine on an exercise machine, the method including the steps of: providing the user with at least one user interface to define the personalized exercise routine; forming machine-readable instructions to control the exercise machine to carry out the exercise routine on the exercise machine, said machine instructions protected as private to the user; storing the personalized exercise routine formed in the machine-readable instructions in a memory device; and user-triggered engaging of the machine-readable instructions to control the exercise machine in carrying out the personalized exercise routine. In the method, the step of forming machine-readable instructions to control the exercise machine can includes the steps of associating the exercise routine with a first exercise machine to produce a first set of signals; and subsequently translating the first set of signals into the machine-readable instructions.

75 Claims, 16 Drawing Sheets

U.S. PATENT DOCUMENTS

| | | | | |
|---|---|---|---|---|
| 5,947,868 | A | 9/1999 | Dugan | 482/4 |
| 5,947,869 | A * | 9/1999 | Shea | 482/8 |
| 5,957,699 | A | 9/1999 | Peterson et al. | 434/350 |
| 6,052,512 | A * | 4/2000 | Peterson et al. | 709/220 |
| 6,059,692 | A | 5/2000 | Hickman | 482/8 |
| 6,458,060 | B1 * | 10/2002 | Watterson et al. | 482/54 |
| 6,527,674 | B1 * | 3/2003 | Clem | 482/8 |
| 6,634,992 | B1 * | 10/2003 | Ogawa | 482/8 |
| 6,635,013 | B2 * | 10/2003 | Pfeffer | 600/300 |
| 6,656,091 | B1 * | 12/2003 | Abelbeck et al. | 482/9 |
| 6,827,669 | B2 * | 12/2004 | Cohen et al. | 482/8 |
| 6,971,973 | B2 * | 12/2005 | Cohen et al. | 482/8 |
| 2002/0077221 | A1 * | 6/2002 | Dalebout et al. | 482/57 |
| 2003/0078786 | A1 * | 4/2003 | Ulrey | 705/1 |
| 2005/0049971 | A1 * | 3/2005 | Bettinger | 705/14.68 |

OTHER PUBLICATIONS http://web.archive.org/web/19990224000954/http://www.cnn.com/TECH/computing/9805/15/workout/.*

"24 Hour Fitness With Netpulse; Members Will Now Get Surfing, TV, Music CDs, News Updates, Sports Scores, and Stock Quotes—All While They Work Out!" Mar. 10, 1998, Business Wire, p. 3100192.*

"Netpulse Selects VITAL Network Services to Help Link Exercise Equipment to the Internet", Oct. 21, 1998, Business Wire, p. 1316.*

Netpulse.com.*

"24 Hour Fitness With Netpulse; Members Will Now Get Surfing, I-V, Music CDs, News Updates, Sports Scores, and Stock Quotes—All While They Work Out!" Mar. 10, 1998, Business Wire, p. 3100192.*

"Netpulse Selects VITAL Network Services to Help Link Exercise Equipment to the Internet", Oct. 21, 1998, Business Wire, p. 1316.*

"UltraCoach HRM", http://fitnessmart.com/fitshopr/products/42172.htm, pp. 1-4.

"PC Coach Elite introduces many new features that enhance your train", www.healthmg.com.au/pc_coach_2000.htm, pp. 1-4.

* cited by examiner

SYSTEM AND METHOD TO IMPROVE FITNESS TRAINING

I. CROSS REFERENCE TO RELATED APPLICATIONS

The present patent application is a continuation-in-part application of U.S. patent application Ser. No. 09/977,557, filed Oct. 15, 2001, now abandoned, and U.S. patent application Ser. No. 09/829,757 filed Apr. 10, 2001, now abandoned. Ser. No. 09/977,557 claims benefit of, and incorporates by reference, Ser. No. 60/270,120 filed Feb. 22, 2011, now expired. Ser. No. 09/829,757 claims benefit from and incorporates by reference, U.S. Patent Application Ser. No. 60/196,498, filed Apr. 12, 2000, now expired. All applications listed above have the same title and all are incorporated by reference.

II. TECHNICAL FIELD OF THE INVENTION

The present invention pertains to an electrical digital computer machine and a data processing system, methods of making and for using the machine, products produced thereby, as well as data structures and articles of manufacture pertaining thereto, as well as all necessary intermediates, all in the field of computerized aspects of machine-based fitness training. More particularly, this invention relates to a digital electrical computer network and methods related thereto for enabling people to program a cardiovascular exercise routine on a personal computer or the like and then have that exercise routine downloaded to a piece of fitness equipment, such as a treadmill. In a more particular embodiment, a virtual private network, or web-based system, makes available a library of preprogrammed exercises, preferably with means for modifying a routine from the library, or for creating a new routine by selecting the type of cardiovascular fitness equipment, the duration of the exercise routine, the number of time intervals, the exercise intensity, and the speed for each interval. Customized routines are stored by the system for future use or reference. Ancillary features for use by a subscriber during a exercise routine are also provided.

III. BACKGROUND OF THE INVENTION

Cardiovascular fitness equipment such as stationary bikes and treadmills, do not allow sufficient customization of the exercise routine by the person training with the equipment. The person exercising is limited to a selection of, say, and just a dozen routines. Some physical fitness experts recommend a particular series of exercise intensity levels for specific time intervals. Physical fitness equipment does not provide an adequate programming interface to customize the exercise routine.

The known interfaces for cardiovascular fitness equipment are cumbersome for inputting data. Usually, the equipment also has a poor input device. Typically a keypad with a few, relatively small buttons is mounted on the cardiovascular fitness machine. The keypad is difficult to manipulate while exercising. For example, it is necessary to focus one's line of vision to a small keypad and press buttons to adjust the parameters of the exercise routine. If this is done while running on a treadmill, the person may lose their sense of balance or mistakenly enter incorrect values.

Typically, the interfacing of cardiovascular fitness equipment has poor graphical presentation and format. Usually the input screen is constructed of a series of LED lights. The graphical interface is uninteresting and does not offer a visually stimulating experience.

The state of the art, prior to the instant invention, cannot be said to be "user friendly." It is to the contrary—limited and cumbersome. Many people are indeed bored while exercising on physical fitness equipment. Perhaps this leads people to read magazines or watch television while exercising on treadmills and stationary bikes, as contrasted with being inspired or even engaged by the equipment. Or worse, the people do not exercise as much because it is not as much fun as other things.

IV. BRIEF SUMMARY OF THE INVENTION

A. Objects of the Invention

The objects and advantages of the present invention are:

It is an object of the present invention to provide a computer system that addresses the prior art issues discussed above.

It is another object of the present invention to provide a method for creating a personalized exercise routine with at least one user interface used in connection with forming machine-readable instructions protected as private to a user subsequently carrying out the exercise routine on an exercise machine.

It is still another object of the invention to provide such a method for providing the user with at least one user interface to define the personalized exercise routine, and/or to control the exercise machine to carry out the exercise routine on the exercise machine, said machine instructions protected as private to the user.

It is yet another object of the present invention to provide a method for storing the personalized exercise routine formed in the machine-readable instructions in a memory device, followed by user-triggered engaging of the machine-readable instructions to control the exercise machine in carrying out the personalized exercise routine.

It is a further object of the present invention to supplement activity pertaining to health improvement by making the time spent using physical fitness equipment more productive.

It is still a further object of the present invention to provide ancillary features, such as Internet-type services, to those exercising on cardiovascular fitness equipment.

It is yet a further object of the present invention to provide capability for checking e-mail, stock prices, and news reports while exercising.

It is yet a further object of the present invention to provide capability for entertainment, such as by seeing horoscopes, reports on topics of interest and hobbies.

It is even more an object of the present invention to provide capability for delivering Internet media to people while they use fitness equipment to improve the value of the time spent while exercising.

B. Summary of the Invention

In accordance with the objects of the present invention, in view of the needs for the invention apparent from elsewhere herein, the present invention includes a computer system that gives people the ability to program a cardiovascular exercise routine on a personal computer and then have that exercise routine downloaded to a piece of fitness equipment, such as a treadmill. Via a virtual private network, and/or a web-based system, a library of preprogrammed exercises is made available in a way that offers users the ability to modify a routine from the library, or to create a new routine by selecting the type of cardiovascular fitness equipment, the duration of the exercise routine, the number of time intervals, the exercise intensity, and the speed for each interval. Customized routines are stored by the system for future use or reference.

The exercise equipment is networked via a virtual private network that provides access, for example, to a host system. The fitness routine is transmitted from the personal computer to the fitness equipment via the network. The personal computer can also be used for obtaining, via communication over the network an agreement to abide by gym rules, such as a contract with an "accept" button on a screen at the personal computer.

In any case, the system loads the fitness program on the controller of the exercise equipment. Further, the system may be capable of "learning" the user's habits and preferences.

A viewable screen and a speaker jack are attached to the exercise equipment. Once the person exercising has initiated the fitness routine, information is presented from the Internet onto the viewable monitor. The format of the display is big and bold so as to be easily viewable by a person exercising. The person exercising can navigate the Internet by browser or in such ways as use a device such as a video game joystick, flexible touch pad on the handles of the equipment, or the browsing experience may be preprogrammed to be hands-free.

The person exercising may choose to use a heart rate monitor and other sensors to measure physical exertion. The system collects data on the heart rate of the person exercising, and data on the actual speed and intensity of the exercise. The system collects data electronically and then stores the data on the system. The system has the ability to allow people to retrieve, manipulate, display, and separately store this data.

More particularly, the foregoing can be carried out by a machine (programmed computer) methods for making and using it, products produced by the method, data structures, and necessary intermediates, collectively referenced herein after as the method (for the sake of brevity). Accordingly the invention can be illustrated as a method for creating a personalized exercise routine with at least one user interface used in connection with forming machine-readable instructions protected as private to a user subsequently carrying out the exercise routine on an exercise machine, the method including the steps of: providing the user with at least one user interface to define the personalized exercise routine; forming machine-readable instructions to control the exercise machine to carry out the exercise routine on the exercise machine, said machine instructions protected as private to the user; storing the personalized exercise routine formed in the machine-readable instructions in a memory device; and user-triggered engaging of the machine-readable instructions to control the exercise machine in carrying out the personalized exercise routine.

Any of the embodiments herein can be carried out with the step of forming machine-readable instructions to control the exercise machine includes the steps of: associating the exercise routine with a first exercise machine to produce a first set of signals; and subsequently translating the first set of signals into the machine-readable instructions.

In another view, a method includes creating a personal exercise routine with at least one user interface for forming machine-readable instructions engaged by a user subsequently carrying out the exercise routine on an exercise machine, the method including the steps of: using the at least one user interface to enable the user to create the personal exercise routine; associating the exercise routine with a first exercise machine to produce a first set of signals; translating the first set of signals into the machine-readable instructions; storing the personal exercise routine formed in the machine-readable instructions in a memory device; and engaging of the machine-readable instructions to control the exercise machine in carrying out the personal exercise routine.

Any of the embodiments herein can be carried out with the step of storing the personal exercise routine includes storing medical information and a charge card number for the user.

Any of the embodiments herein can be carried out by including the step of: forming a profile of the user; and protecting the profile of the user as private to the user, along with said machine-readable signals.

Any of the embodiments herein can be carried out by including the step of: forming a profile of the user; and protecting the profile of the user as private to the user, along with said machine-readable signals.

Any of the embodiments herein can be carried out with a computer network that provides users the ability to program a cardiovascular exercise routine on a personal computer and download the programmed routine to a piece of fitness equipment.

Any of the embodiments herein can be carried out with a virtual private network, the web-based system makes available a library of modifiable preprogrammed exercises and routines.

Any of the embodiments herein can be carried out with a customized routine creatable by selecting a type of cardiovascular fitness equipment, the duration of an exercise routine, a number of time intervals, exercise intensity, and a speed for each interval.

Any of the embodiments herein can be carried out with a customized routine stored by the system for future use or reference.

Any of the embodiments herein can be carried out with the customized routine added to the library.

Any of the embodiments herein can be carried out such that users who are not gym subscribers to the system can walk in to a gym and swipe a credit card or smart card for access to the system.

Any of the embodiments herein can be carried out with a card reader on the exercise equipment and/or at a reception desk.

Any of the embodiments herein can be carried out such that users must check availability of exercise equipment and acknowledge agreement with gym rules and regulations on a personal computer.

Any of the embodiments herein can be carried out with online purchases that can be made using the system, e.g., by swiping a credit card.

Any of the embodiments herein can be carried out with personal profiles transferable between gyms utilizing the same system or linked systems.

Any of the embodiments herein can be carried out with exercises that use multiple types of exercise equipment.

Any of the embodiments herein can be carried out with customized video, TV, or electronic magazines for the user.

Any of the embodiments herein can be carried out with the user enabled to shop while exercising.

Any of the embodiments herein can be carried out with the user enabled to view e-mail, stock prices, and/or news reports while exercising.

Any of the embodiments herein can be carried out with the user entertained by viewing horoscopes, and/or reports on topics of interest and hobbies, presented via the system.

Any of the embodiments herein can be carried out with Internet media delivered to users while using cardiovascular fitness equipment.

Any of the embodiments herein can be carried out with a cardiovascular exercise routine programmed on a personal computer and downloaded to a piece of fitness equipment.

Any of the embodiments herein can be carried out with the exercise equipment networked via a virtual private network that provides access to a host system.

Any of the embodiments herein can be carried out with the fitness routine transmitted from the personal computer to the fitness equipment via the network.

Any of the embodiments herein can be carried out with the system loading the fitness program into the controller of the exercise equipment.

Any of the embodiments herein can be carried out with a viewable monitor and a speaker jack provided on the exercise equipment.

Any of the embodiments herein can be carried out with information form the Internet presented via the viewable monitor.

Any of the embodiments herein can be carried out with the user navigating the Internet while exercising by use of a device such as a video game joystick, flexible touch pad on the handles of the equipment, or the browsing experience preprogrammed to be hands-free.

Any of the embodiments herein can be carried out with hands-free programming allowing the user to select the content and presentation format at a time prior to beginning the exercise routine.

Any of the embodiments herein can be carried out with the user exercising choosing to use a heart rate monitor and/or other sensors to measure physical exertion.

Any of the embodiments herein can be carried out with the system collecting data on the heart rate of the user exercising, and data on the actual speed and intensity of the exercise routine.

Any of the embodiments herein can be carried out with the system collecting data electronically and then storing the data in system memory.

Any of the embodiments herein can be carried out with the system allowing users to separately retrieve, manipulate, display, and store the data.

Any of the embodiments herein can be carried out with a treadmill equipped with a display screen, a joystick control, and a heart rate monitor sensor.

Any of the embodiments herein can be carried out with the treadmill equipped with a viewable monitor display, a numeric keypad, a joystick, input devices equipped with buttons and touch pad, a heart rate monitor, a hand held control unit with buttons, and a magnetic strip card reader.

Any of the embodiments herein can be carried out with the users using a calendar function to schedule a particular piece of exercise equipment for an individual date or series of dates.

Any of the embodiments herein can be carried out with the users using a calendar function to schedule a use of a group of pieces of exercise equipment, and order of use, for an individual date or series of dates.

Any of the embodiments herein can be carried out with a exercise schedule created by the system for the individual, and stored electronically on a computer or on a disk for non-networked machines.

Any of the embodiments herein can be carried out with the schedule indicating a group of pieces of exercise equipment, and order of use, for an individual date or series of dates, for one person or a group of people.

Any of the embodiments herein can be carried out with the system downloading parameters of an exercise routine to a particular piece of exercise equipment when the user identifies himself to the system.

Any of the embodiments herein can be carried out with the system configuring the cardiovascular fitness equipment of a gym on a virtual private network.

Any of the embodiments herein can be carried out with the fitness equipment configured with a display monitor to allow viewing of Internet-type media.

Any of the embodiments herein can be carried out with the cardiovascular fitness equipment having connectivity to a virtual private network that provides access to a host system.

Any of the embodiments herein can be carried out with a user of the system having the ability to logon to the virtual private network from a personal computer that has connectivity via a modem or like technology.

Any of the embodiments herein can be carried out with connectivity to the world wide web, or public Internet provided via the host system.

Any of the embodiments herein can be carried out with the user surfing the Internet while exercising on the fitness equipment.

Any of the embodiments herein can be carried out with the fitness equipment having computer screen.

Any of the embodiments herein can be carried out with software providing a web browser interface on the computer screen of the exercise equipment.

Any of the embodiments herein can be carried out with information presented from the Internet onto the computer screen of the exercise equipment.

Any of the embodiments herein can be carried out with text, audio, and graphical information presented on a variety of subjects in the form of news, entertainment, financial market data, weather reports, electronic mail, shopping, and advertising, among other subjects.

Any of the embodiments herein can be carried out with the system providing access to all types of subjects and types of information available on the Internet.

Any of the embodiments herein can be carried out with the format of the display preferably big and bold so as to be easily viewable by the user while exercising.

Any of the embodiments herein can be carried out with the user navigating, or "surfing", the Internet by use of an interface such as a video game joystick while exercising.

Any of the embodiments herein can be carried out with hands-free surfing available, with the browsing being preprogrammed to automatically change screens.

Any of the embodiments herein can be carried out with parameters of the fitness routine including the type of equipment, the duration of the session, the intensity level, and a pattern of variation of the intensity level.

Any of the embodiments herein can be carried out with the system collecting and storing the electronic data obtained by a sensor.

Any of the embodiments herein can be carried out with sensor data retrieved, manipulated, displayed, and formatted into reports using a personal computer and the host system.

Any of the embodiments herein can be carried out with the reports stored for future reference.

Any of the embodiments herein can be carried out with reports shared with other persons computers at the discretion of the user.

Any of the embodiments herein can be carried out with all types of cardiovascular fitness equipment accommodated by the system.

Any of the embodiments herein can be carried out with the cardiovascular equipment comprising one of at least a treadmill, an elliptical trainer, a stationary bike, a stationary ski machine, a stationary rowing machine, and resistance type equipment.

Any of the embodiments herein can be carried out with the virtual private network including one or many gym sites.

Any of the embodiments herein can be carried out with each gym site housing either a single type of exercise equipment or a variety of types of equipment.

Any of the embodiments herein can be carried out with a multitude of personal computers accommodated by the virtual private network.

Any of the embodiments herein can be carried out with a single or several host systems available depending upon geography, functionality, and networking technology.

Any of the embodiments herein can be carried out with the fitness equipment in the user's own home, at a gym or spa, at the exercise facility of an apartment complex, hotel, or motel.

Any of the embodiments herein can be carried out with the virtual private network as a network of computer devices in which access is controlled by assigning a user identification name and a password to each device, which may be a unique network or part of other private networks, including at least America Online, and Prodigy, or the like.

Any of the embodiments herein can be carried out with the system operating over the world wide web.

Any of the embodiments herein can be carried out with a home gym having no connectivity to any type of computer network is accommodated.

Any of the embodiments herein can be carried out with an operator of a host system performing all tasks necessary to create, populate, and maintain a business operations database.

Any of the embodiments herein can be carried out with the business operations database containing information on gym sites, quantity and types of fitness equipment at each site, and parameters of exercise routines.

Any of the embodiments herein can be carried out with an operator of a host system creating and maintaining a client profile database containing a profile for each user subscribing to the system.

Any of the embodiments herein can be carried out with users provided access to a virtual private network to select an exercise routine to be performed during a future exercise session.

Any of the embodiments herein can be carried out with text and graphics provided through a web browser interface to describe the parameters of an exercise routine.

Any of the embodiments herein can be carried out with the user prompted to choose an exercise from the library.

Any of the embodiments herein can be carried out with the user customizing a routine from the library.

Any of the embodiments herein can be carried out with a user creating a unique routine.

Any of the embodiments herein can be carried out with parameters of customized exercise routines, including information on type of equipment, duration of the exercise, and level and pattern of intensity, stored by the system.

Any of the embodiments herein can be carried out with a controller of the exercise equipment controlled by the exercise parameters.

Any of the embodiments herein can be carried out with system users accessing the virtual private network to schedule the exercise session, through a web browser interface, selecting the location, date, and time the exercise routine to be accomplished.

Any of the embodiments herein can be carried out with users accessing the virtual private network to configure web viewing through a web browser interface, configuring screens of the web browser, which is part of the exercise equipment, and selecting types of content to be viewed while exercising, via the virtual private network.

Any of the embodiments herein can be carried out with users initiating an exercise session by mounting a piece of exercise equipment and presenting identification by keying in an identification name and password on a keypad, or through alternative technology such as a smart card or magnetic strip card reader.

Any of the embodiments herein can be carried out with visual and audio Internet media including but not limited to: reading and responding to E-mail; reviewing and receiving messages from a paging service; viewing weather reports; viewing airport travelers report; viewing national news reports; viewing local news reports; checking stock quotes; viewing sports reports; listening to music; viewing music videos; viewing a fashion make-over; checking movie reviews and listings; checking entertainment news and reports; reading book reviews; participating in chat rooms; reviewing job postings; viewing vacation literature; reviewing exercise tips; and shopping online.

Any of the embodiments herein can be carried out with data on heart rate, speed, intensity level, and duration of the exercise session collected and stored by the system.

Any of the embodiments herein can be carried out with management tools for exercise data are provided by the system.

Any of the embodiments herein can be carried out with users reviewing exercise data and Internet content from pervious exercise sessions.

Any of the embodiments herein can be carried out with the user enabled to view and configure reports to display data including intensity levels of the exercise routine and heart rate through a web browser interface.

Any of the embodiments herein can be carried out with a user and an operator of a host system gaining access to the virtual private network to conduct consultations.

Any of the embodiments herein can be carried out with tool sets offered to gym owners, the manufacturers of fitness equipment, personal trainers, doctors, and users allowing analysis of data collected and stored by the system to improve user fitness, to optimize the utilization of the gym's assets, to enhance consultation by personal trainers and medical professionals, and for use in improving the design and performance of fitness equipment, through a web browser interface.

Any of the embodiments herein can be carried out with an operator of a host system creating, populating, and maintaining a library of exercise routines.

Any of the embodiments herein can be carried out with a set of parameters for each type of fitness equipment input into a database, the parameters including duration of an exercise session, intensity level, and pattern of intensity.

Any of the embodiments herein can be carried out with the pattern in a wavelike profile, a profile steadily increasing then steadily decreasing, or a simulation of a race on an actual racecourse or on a fictitious racecourse.

Any of the embodiments herein can be carried out with the exercise routine accompanied by video, audio, or text messages to simulate an actual running event.

Any of the embodiments herein can be carried out with the fitness routine library of the system allowing programming of exercises in advance, prior to a user mounting and using the fitness equipment.

Any of the embodiments herein can be carried out with access to the fitness routine library obtained via a web-based system via a virtual private network.

Any of the embodiments herein can be carried out such that a user can choose from an assortment of preprogrammed exercises in the library.

Any of the embodiments herein can be carried out such that an operator of a host system creates a resource pool database of available exercise equipment.

Any of the embodiments herein can be carried out such that the database also contains information on gym sites that are part of the virtual private network.

Any of the embodiments herein can be carried out such that the database also contains information on the quantity and types of fitness equipment at each gym site.

Any of the embodiments herein can be carried out such that the operator of the host system creates and maintains a resource pool database of personal trainers and medical professionals qualified to advise clients on diet, nutrition, and exercise or training.

Any of the embodiments herein can be carried out such that the operator of the host system creates and maintains a client profile database wherein the profile for each user includes at least name, e-mail address, mailing address, and telephone number.

Any of the embodiments herein can be carried out such that the system assigns a unique user identification name and password to each user.

Any of the embodiments herein can be carried out such that the user logs on to the system and reviews profile information and revises information via a web browser interface, by inputting a subscriber identification number and password to gain access to the personal account of the user.

Any of the embodiments herein can be carried out such that the user inputs personal information including birth date, gender, weight, height, body fat composition, and health history.

Any of the embodiments herein can be carried out such that the user is prompted to indicate any gym membership, or if a home gym is available.

Any of the embodiments herein can be carried out such that, if a gym membership exists, the name of gym, the gym location, and the gym membership identification number are input by the user.

Any of the embodiments herein can be carried out such that the system can locate a gym within an area of residence, business, or travel destination.

Any of the embodiments herein can be carried out such that the user gains access to the virtual private network via a personal computer in order to select an exercise routine to perform at some future time.

Any of the embodiments herein can be carried out such that the user selects an exercise routine at the beginning of exercising, via the input device on the exercise equipment.

Any of the embodiments herein can be carried out such that the user selects the type of exercise equipment through a web browser interface.

Any of the embodiments herein can be carried out such that text and graphics are used to describe parameters of the exercise through a web browser interface.

Any of the embodiments herein can be carried out such that the system prompts the user to choose exercise parameters from the library.

Any of the embodiments herein can be carried out such that the user customizes a routine from the library, or creates a unique routine and stores those routine parameters on the system if none of the preprogrammed routines in the library are satisfactory.

Any of the embodiments herein can be carried out such that the parameters of the exercise routines, including type of equipment, duration of exercise, and level and pattern of intensity, are stored electronically by the system.

Any of the embodiments herein can be carried out such that a controller of the exercise equipment is loaded with the exercise parameters.

Any of the embodiments herein can be carried out such that the controller controls function of a treadmill motor, driving a belt of the treadmill, and an actuator that increases or decreases incline of the treadmill, and any other related input/output devices.

Any of the embodiments herein can be carried out such that the user delegates this function to a personal trainer or medical professional.

Any of the embodiments herein can be carried out such that the users of the system gain access to the virtual private network to schedule the exercise session.

Any of the embodiments herein can be carried out such that the user selects the location, date, and time an exercise routine through a web browser interface.

Any of the embodiments herein can be carried out such that the user delegates this function to a travel agent, a personal trainer, or medical professional.

Any of the embodiments herein can be carried out such that the user selects a exercise location.

Any of the embodiments herein can be carried out such that the exercise location may be the user's home, a gym, or a spa that is part of the virtual private network.

Any of the embodiments herein can be carried out such that the user chooses a date and time for the exercise routine.

Any of the embodiments herein can be carried out such that the system allows one exercise session, multiple exercise sessions, or a recurring session to be scheduled.

Any of the embodiments herein can be carried out such that scheduled routines are synchronized with a calendar function of an electronic personal information manager.

Any of the embodiments herein can be carried out such that the system confirms that exercise equipment is available and electronically notify the user, or confirm on an electronic calendar of the user.

Any of the embodiments herein can be carried out such that, in the event that there is a conflict with availability of exercise equipment or an event on the calendar of the electronic personal information manager, the user is prompted to resolve the conflict.

Any of the embodiments herein can be carried out such that users gain access to the virtual private network to configure web viewing.

Any of the embodiments herein can be carried out such that, through a web browser interface, the user configures the screens of the web browser and selects the types of content for viewing while exercising via the virtual private network.

Any of the embodiments herein can be carried out such that users use the system to select the type of Internet material to be presented during their exercise.

Any of the embodiments herein can be carried out such that the user configures the display on the exercise equipment to have split screens.

Any of the embodiments herein can be carried out such that the screen may be split to show a variety of information at one time.

Any of the embodiments herein can be carried out such that the user selects the method for web browsing.

Any of the embodiments herein can be carried out such that the user has the option to program "hands free surfing", or the option to use input devices.

Any of the embodiments herein can be carried out such that wherein stock is traded while exercising online.

Any of the embodiments herein can be carried out such that the system provides an option to allow the user to select the order in which web subject content is provided, the duration of each presentation, and the option to not display sensitive or confidential information.

Any of the embodiments herein can be carried out such that the user chooses whether or not to have a selection of online services presented for a predetermined interval.

Any of the embodiments herein can be carried out such that the duration of the display interval may be scaled based upon the speed or intensity of the exercise level or the interval may be determined by direct user input.

Any of the embodiments herein can be carried out such that the user chooses which topics will be presented during the exercise routine.

Any of the embodiments herein can be carried out such that the user chooses the type of Internet material that is to be displayed during exercise.

Any of the embodiments herein can be carried out such that the user chooses whether or not to have audio media presented during the exercise routine.

Any of the embodiments herein can be carried out such that the user begins the exercise session.

Any of the embodiments herein can be carried out such that the user mounts a treadmill and enters identifying information to the system either by keying in an identification name and password, or using some other type of technology such as a smart card or magnetic strip card reader.

Any of the embodiments herein can be carried out such that the user chooses whether or not to connect to a heart rate monitor or other device to collect vital signs.

Any of the embodiments herein can be carried out such that the system loads the exercise parameters into the controller of the exercise equipment based upon user preference.

Any of the embodiments herein can be carried out such that wherein the system directs visual and audio media to the user.

Any of the embodiments herein can be carried out such that online services include: receive, review, and respond to E-mail; review and receive messages from a paging service; view weather reports; view airport travelers report; view national news reports; view local news reports; check stock quotes; view sports reports; listen to music; view music videos; view a fashion make-over; check movie reviews and listings; check entertainment news and reports; see book reviews; participate in chat rooms; review job postings; see vacation literature; review exercise tips; make reservations for restaurants; and shop online.

Any of the embodiments herein can be carried out such that the system collects and stores data on the heart rate, speed, intensity level, and duration of the exercise.

Any of the embodiments herein can be carried out such that the system monitors the actual speed and intensity of resistance for the user while exercising.

Any of the embodiments herein can be carried out such that speed and intensity data is used as an input to a video game or virtual race.

Any of the embodiments herein can be carried out such that video images of a course are programmed to be synchronized with the speed and incline of a belt of the exercise equipment.

Any of the embodiments herein can be carried out such that Internet content is delivered to the user, but is not personalized.

Any of the embodiments herein can be carried out such that the system downloads the parameters of the exercise routine to the fitness equipment that is part of the virtual private network.

Any of the embodiments herein can be carried out such that the system allows the user to change the intensity of the exercise, during the exercise session by using a keypad or other input device.

Any of the embodiments herein can be carried out such that Internet content may be programmed to turn off so as to not disturb the person exercising at a peak moment.

Any of the embodiments herein can be carried out such that the system allows the user to pause and restart exercise routines.

Any of the embodiments herein can be carried out such that the system stores data during a pause.

Any of the embodiments herein can be carried out such that heart rate data and other vital statistics are collected and stored electronically by the system.

Any of the embodiments herein can be carried out such that users access to the virtual private network to review exercise data and Internet content from previous exercise sessions.

Any of the embodiments herein can be carried out such that exercise routines and exercise sessions are scheduled for the users group as a single entity.

Any of the embodiments herein can be carried out such that users belong to one or several groups Any of the embodiments herein can be carried out such that the system allows users to share access to their exercise data with others including users friends, doctors, personal trainers, and physical therapist.

Any of the embodiments herein can be carried out such that the user initiates the programmed routine exercise.

Any of the embodiments herein can be carried out such that the system provides the gym owner reports and graphical tools to quantify the usage of each piece of fitness equipment.

Any of the embodiments herein can be carried out such that the system creates reports relating populating of the various pieces of equipment to show which type of equipment is most popular trends in preference, and user exercise habits over a range of time.

Any of the embodiments herein can be carried out such that the system tracks attendance of users with reservations.

Any of the embodiments herein can be carried out such that the system provides attendance records of the users to the gym personnel.

Any of the embodiments herein can be carried out such that the system manages gym membership or interfaces with an existing system.

Any of the embodiments herein can be carried out such that the system tracks fees and dues owed by gyms users, issues invoices, and manages account balances.

Any of the embodiments herein can be carried out such that the system allows gym users to view their account status and balance.

Any of the embodiments herein can be carried out such that the operator of the host system may delegate all or partial responsibility for maintaining and operating the system.

Any of the embodiments herein can be carried out such that an existing virtual private network such as America Online or Prodigy may be contracted to operate the system.

Any of the embodiments herein can be carried out such that a switch device is used to network the devices at a site.

Any of the embodiments herein can be carried out such that a network may contain one or more switches per site for local area connectivity.

Any of the embodiments herein can be carried out such that a router is used for wide area connectivity to the virtual private network.

Any of the embodiments herein can be carried out such that, in the event that the wide area connectivity or any part of the local area network is not operating, the treadmill is able to operate based on a set of default exercise parameters, or from a disk.

Any of the embodiments herein can be carried out such that preprogrammed fitness routines and Internet-type media are stored in memory that is part of, or accessible by, the controller of the fitness equipment.

Any of the embodiments herein can be carried out such that the name of the gym in which the fitness equipment is physically located appears on the display monitor.

Any of the embodiments herein can be carried out such that the gym name is a hyperlink to the home web site of the gym.

Any of the embodiments herein can be carried out such that the name of the user appears on the display monitor.

Any of the embodiments herein can be carried out such that the week for which the user plans an exercise routine appears on the display monitor.

Any of the embodiments herein can be carried out such that the days of the week are listed in boxes at the bottom of the display monitor on the tabs.

Any of the embodiments herein can be carried out such that arrows to each side of the day boxes are used to view the next week, by clicking the right arrow button, or the previous week, by clicking the left arrow button.

Any of the embodiments herein can be carried out such that the day boxes form a hyperlink to the calendar function of the personal information manager of the client or gym.

Any of the embodiments herein can be carried out such that an input box for the selecting a duration of an exercise routine appears on the display monitor.

Any of the embodiments herein can be carried out such that the input box provides a dropdown menu selection.

Any of the embodiments herein can be carried out such that a start time box for the exercise routine appears on the display monitor.

Any of the embodiments herein can be carried out such that dropdown menu selection.

Any of the embodiments herein can be carried out such that the start time box provides an equipment selection appears on the display monitor.

Any of the embodiments herein can be carried out such that equipment selection input box provides a dropdown menu that listing the equipment of the named gym.

Any of the embodiments herein can be carried out such that use of a heart rate monitor is selectable.

Any of the embodiments herein can be carried out such that a monitor selection activates a hyperlink to a site containing health-monitoring reports.

Any of the embodiments herein can be carried out such that a speed over time profile of the planned exercise routine appears on the display monitor.

Any of the embodiments herein can be carried out such that the profile displayed may be modified.

Any of the embodiments herein can be carried out such that adjustable characteristics of the fitness equipment are adjustable by the user.

Any of the embodiments herein can be carried out such that a user, trainer, or medical professional inputs known health risks of the person to be exercising.

Any of the embodiments herein can be carried out such that the system develops a training plan is performed through input from a trainer or by means of a programmed algorithm.

Any of the embodiments herein can be carried out such that the developed training plan outputs a exercise schedule.

Any of the embodiments herein can be carried out such that the schedule is comprised of exercises from a stored library.

Any of the embodiments herein can be carried out such that the exercise schedule includes exercises not performed on a networked exercise device.

Any of the embodiments herein can be carried out such that a magnetic card reader is part of the network and preferably is mounted to the exercise equipment.

Any of the embodiments herein can be carried out such that the user logs onto the system by passing a magnetic strip card through the card reader.

Any of the embodiments herein can be carried out such that a processor of the exercise equipment and accesses the exercise schedule for the user via a server.

Any of the embodiments herein can be carried out such that the host downloads, from a server, to the processor of the exercise equipment, the appropriate exercise parameters.

Any of the embodiments herein can be carried out such that the exercise library stored on a file server that is part of the system.

Any of the embodiments herein can be carried out such that data is processed, to produce a exercise schedule.

Any of the embodiments herein can be carried out such that the exercise schedule references exercise routines that are stored on the network and controls an exercise equipment processor to set characteristics of the equipment appropriately based on the stored routines.

The foregoing, in any combination, summarizes the invention set forth below in a detailed and representative embodiment.

V. BRIEF DESCRIPTION OF THE DRAWINGS

Figure 14:
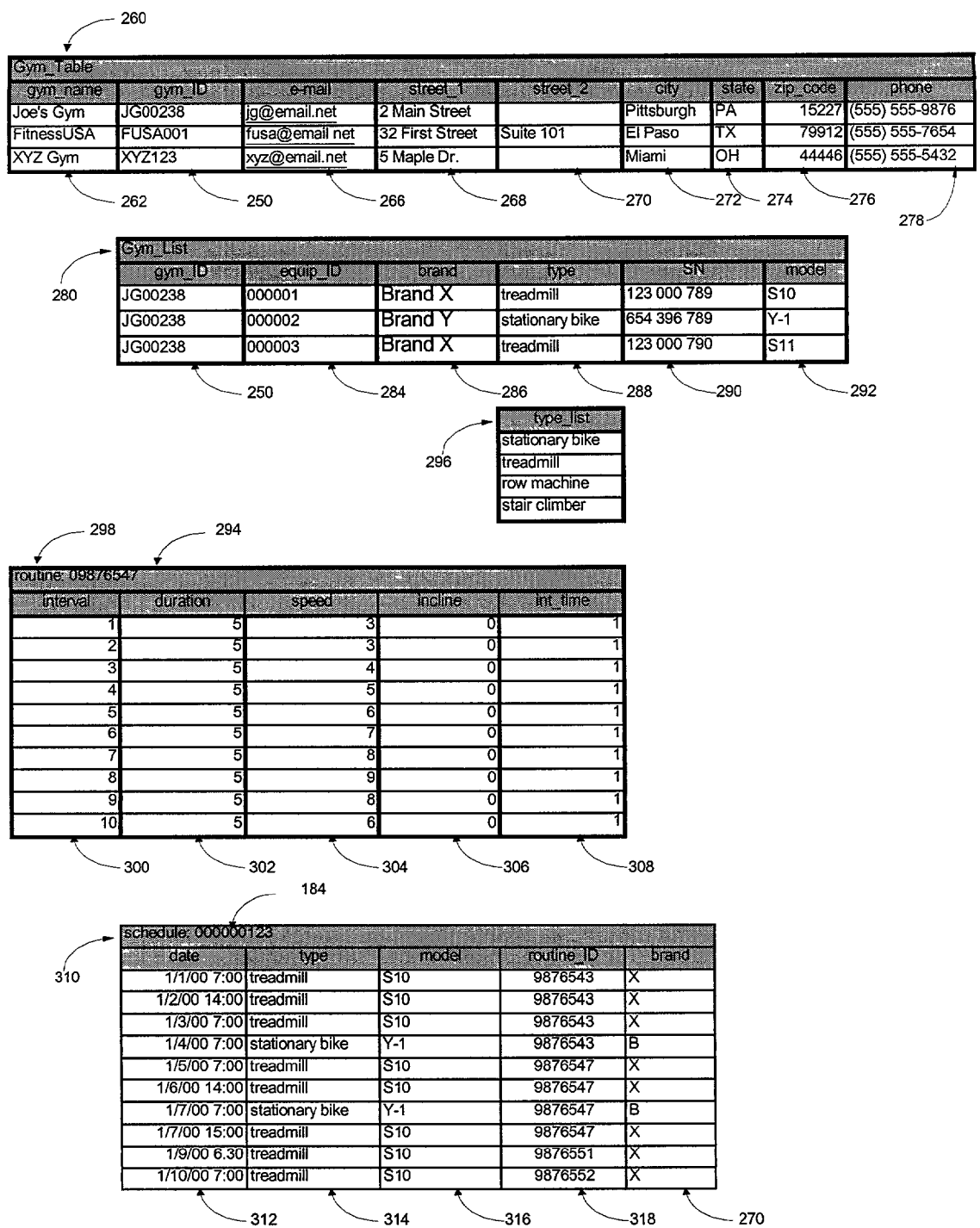

FIG. 14 displays the tables for managing the data of the gyms and equipment.

Figure 15:
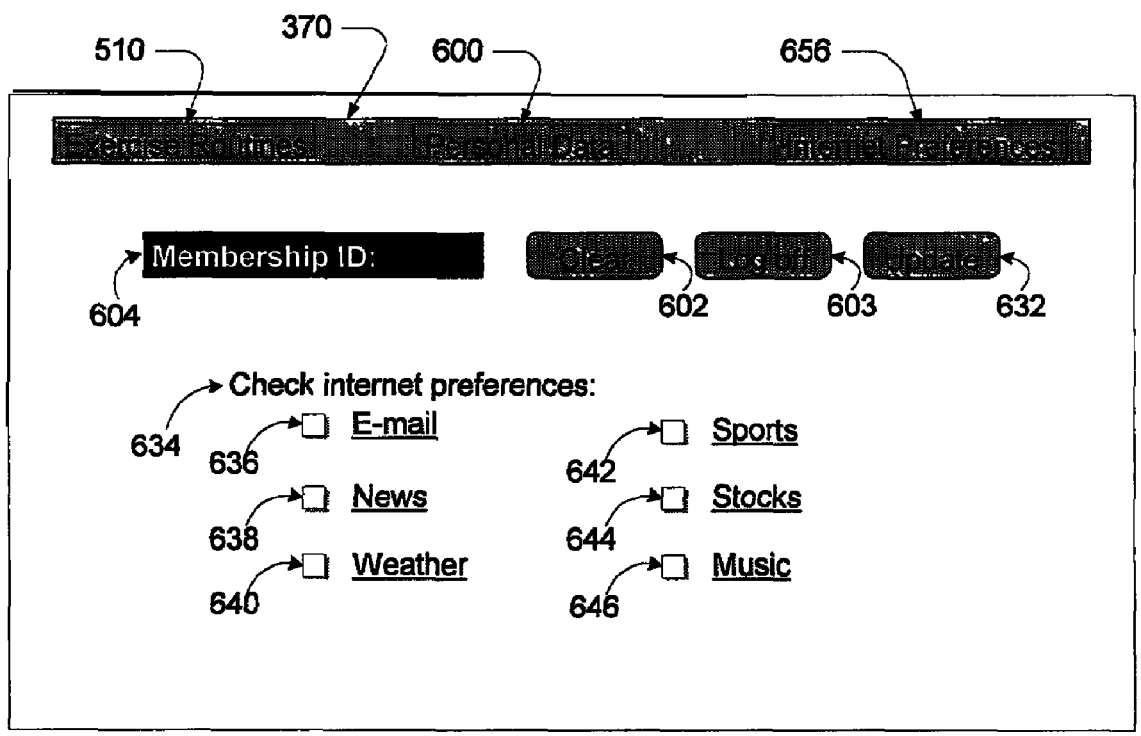

FIG. 15 shows an interface screen to update Internet preferences.

Figure 16:
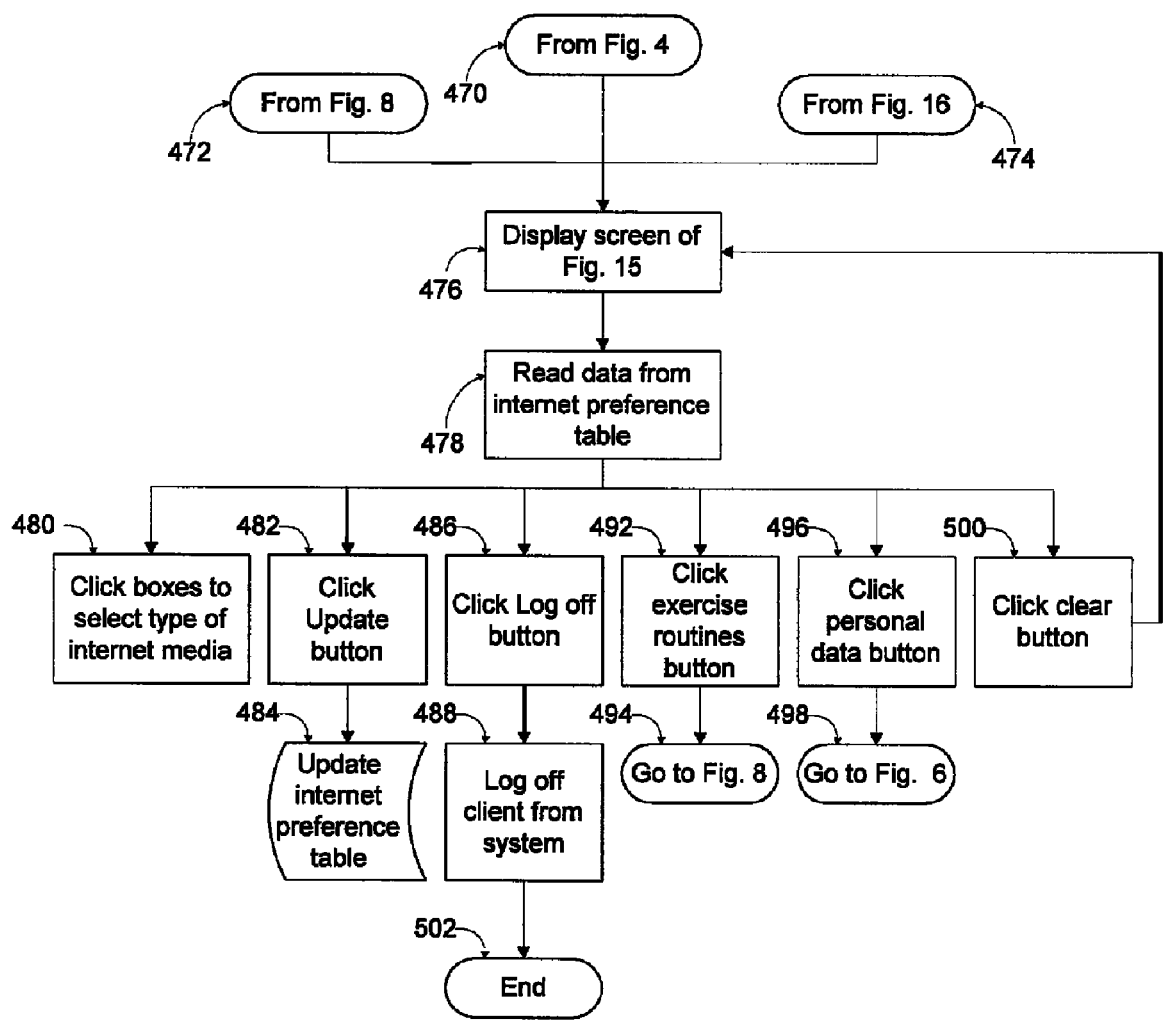

FIG. 16 is a flowchart of activities describing how to update Internet preferences.

VI. DETAILED DESCRIPTION OF THE DRAWINGS

Figure 1:
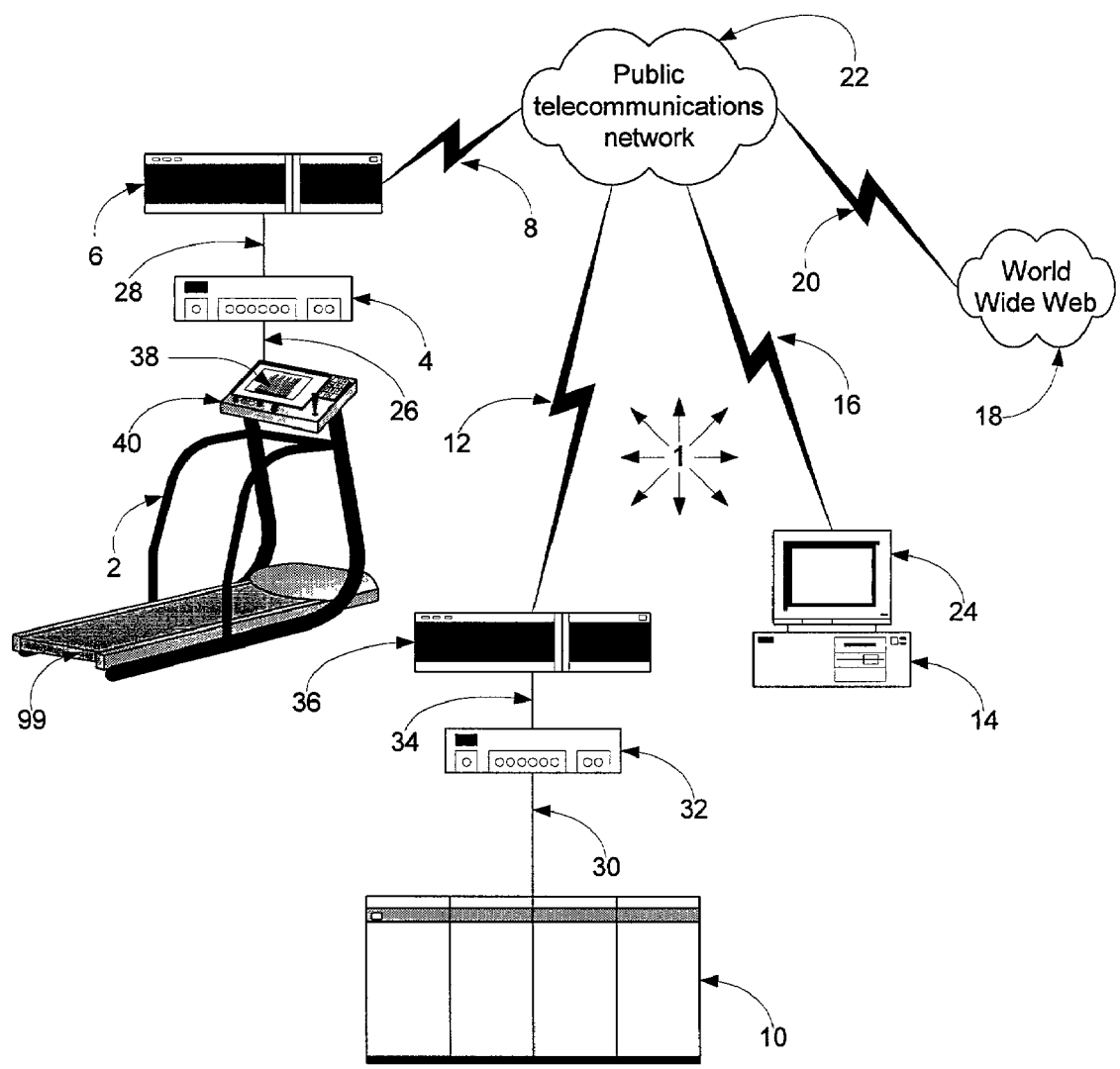
FIG. 1 is a diagram of a computer network for the method.

FIG. 1 represents the preferred embodiment of the present invention. By way of an overview, FIG. 1 provides a diagram for the present invention. A piece of exercise equipment 2, for example has a computer 40, with a display screen 38 that is connected to switch device 4 by a cable 26. The switch 4 is connected to a router 6 by a cable 28. The router has connectivity 8 to the public telecommunications network 22 via an Internet service provider. A home personal computer 14, with monitor 24, has connectivity 16 to the public telecommunications network 22 via an Internet service provider. The host system 1 also has connectivity to the public telecommunications network 22, via a cable 30, a switching device 32, another cable 34, a router 36, and a connection 12 by an Internet service provider. There is also connectivity 20 to the World Wide Web 18 via a system managed by the telecommunications companies.

The system 1 configures the cardiovascular fitness or exercise equipment 2 of a gym on the public telecommunications network 22. The cardiovascular fitness equipment 2 has connectivity 8 to a public telecommunications network 22 that provides access to a host system 1 and is otherwise shown in FIG. 1.

A subscriber of this system 1 has the ability to log on to the system 1 from a personal computer 14 that has connectivity 16 via a modem or like technology. Connectivity 20 to the World Wide Web 18, or public Internet is provided via a public telecommunications network 22, and can include a linkage with host system 1, as illustrated for in an exemplary manner in FIG. 1.

The subscriber can view Internet media while exercising on a treadmill 2 via the display monitor 38. Software is used to provide a web browser interface on the display monitor 38 of the exercise equipment 2.

The browser interface is a very important part of the present invention in embodiments carried out at a gym or other such facility. The browser interface may, for GEL example, begin with a screen identifying the gym, such as "WELCOME TO GOLD'S GYM." The browser interface operates intermediate a web browser and the exercise equipment in linking the user and local activity to the Internet, as well as in carrying out user profile instructions, flags, filters, and the like. Text, audio, and graphical information may be presented on a variety of subjects, such as: news, entertainment, financial market data, weather reports, electronic mail, shopping, and advertising. The present invention is not limited to the subjects of information listed; the system 1 provides access to all subjects of types and all information that are available on the Internet. Preferably the format of the display is bigger than usual and bold so as to be easily viewable by the subscriber while exercising. To navigate the Internet, an interface device such as a video game joystick 100 is provided. Hands-free surfing is also available, the browsing being preprogrammed with screens changing automatically. Such programming is carried out using said profile, and coordination of the screens on the monitor or other such display device with the exercise routine. That is, if one were to program a series of screens or sites only by time, and the routine were to be completed more quickly, then the programming would be inappropriate in duration. While a cut off button on the screen can terminate the presentation, coordination is a preferred feature.

The interface can also be used in accessing a virtual private network of, say, a gym, in scheduling an exercise session by selecting and reserving the location, date, and time the exercise routine is to be accomplished. And as is further discussed herein, the browser interface also is used in configuring web viewing, including configuring screens of the web browser (preferably stored on the exercise equipment), and including selecting types of content to be viewed while exercising.

This system 1 gives people the ability to program a cardiovascular exercise routine on a personal computer 14 and then have those exercise routine parameters input into the computer 40 of the cardiovascular fitness equipment. The computer 40 is a programmable electronic device that controls the function of the equipment, such as setting the speed of the motor 95 that drives the treadmill belt 99, see FIG. 3.

The present invention applies to all types of fitness equipment, particularly cardiovascular equipment, including but not limited to treadmills 2, elliptical trainers, stationary bikes, stationary ski machines, and stationary rowing machines. The present invention also applies to resistance type of equipment, such as weight lifting machines.

The public telecommunications network 22 may accommodate one or many gym sites; each gym may house a single type of exercise equipment or a variety of types of equipment. A multitude of personal computers 14 may be connected to the public telecommunications network 22.

There may be a single host system 1 or several host systems, depending upon geography, functionality, and networking technology.

The scope of the invention includes fitness equipment regardless of the nature of the facility in which the fitness equipment is located. The fitness equipment may be in one's own home, at a gym or spa, the exercise facility of an apartment complex, hotel, or motel, etc.

The present invention also applies to a home gym that has no connectivity to any type of computer network.

The words "subscriber(s)", "client(s)" and "user(s)" are used in this document to refer to people that have access to the system 1.

Figure 2:
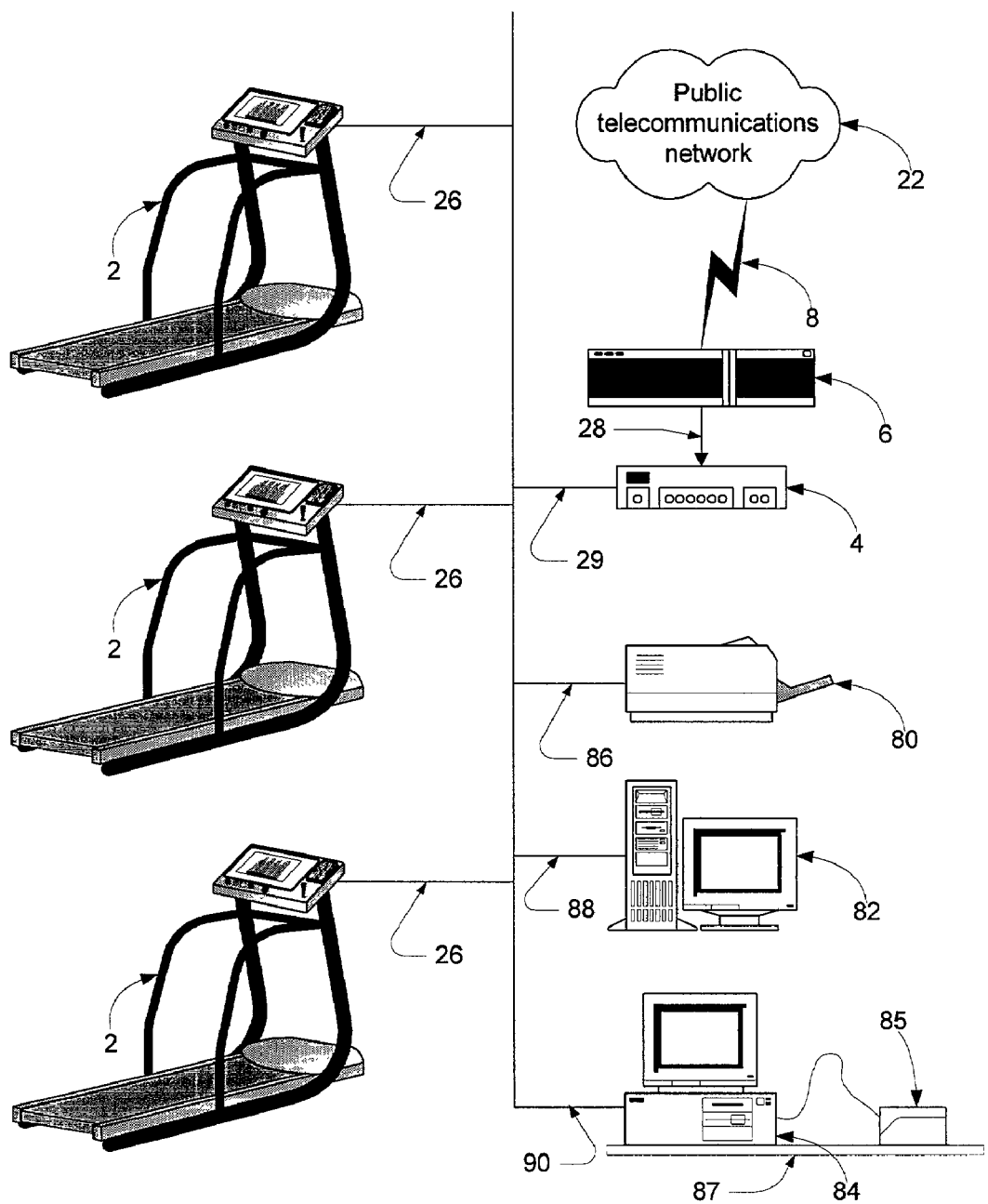
FIG. 2 represents a local area network of a gym, including the exercise equipment.

FIG. 1 and FIG. 2, by way of an overview, illustrates a network of a gym. The network includes several pieces of exercise equipment 2, each connected to a switch 4 via a cable 26. A personal computer 84 is connected to the switch 4 by a cable 90. The employees or the customers of the gym may use the computer to access the system 1. Customers may make modifications to their exercise routines or print a copy of their schedule on the printer 80, which is connected to the switch 4 by a cable 86. The server 82 is connected to the network by a cable 88. The server 82 is used to store exercise routines 298 and schedules 310.

The switch 4 of the gym network is connected to the public telecommunications network 22, via a cable 28, a router 6, and a connection 8 provided by an Internet service provider.

The invention may use wireless connections instead of hard wired connections shown as items 26, 29, 86, 88, and 90.

FIG. 2 shows only treadmills 2 but the system 1 may include a variety of different types of fitness equipment. A personal computer 84 is part of the network so that clients, personnel and management of the gym can have access to the system 1. More than one personal computer 84 may be connected to this network for any given site. A server computer 82 is used to administer programs, store data, and perform network administration functions. Here or elsewhere accessible over the network 22, one can store or attend to all the tasks necessary to create, populate, and maintain a business operations database, including knowing what kinds of exercise equipment is at each site, and information for translating a routine on one machine into a routine for another. The business operations database contains information on gym sites, quantity and types of fitness equipment at each site, and parameters of exercise routines. Over the network 22, e.g., by server access, one can also conduct a search for an exercise facility entering an indicator, such as a zip code, equipment type, city, or other such location indicator, enabling a database search to find at least one suitable facility.

More than one server computer 82 may exist on the network per site. A printer 80 is present to print schedules and reports of the exercise sessions for the use of the clients, personnel and management of the gym. A switch device 4 is used to network the devices at a site. A network may contain one or more switches 4 per site for local area connectivity. A router 6 is used for wide area connectivity 8 to the public telecommunications network 22.

In the event that the wide area connectivity 8 or any part of the local area network or wide area network is not operating, the treadmill 2 is operable based on a set of default exercise parameters, from a disk, or from a server. Preprogrammed fitness routines and Internet-type media are stored in memory that is part of the controller of the fitness equipment 2.

Note that a disk can be used too as memory means transported to an exercise machine for reading (signals representing the exercise routine) by the exercise machine.

Item 85 represents a card reader. Item 87 represents the reception desk at a gym as an exemplary admission control system, regulating access to the facility and/or equipment.

Figure 3:
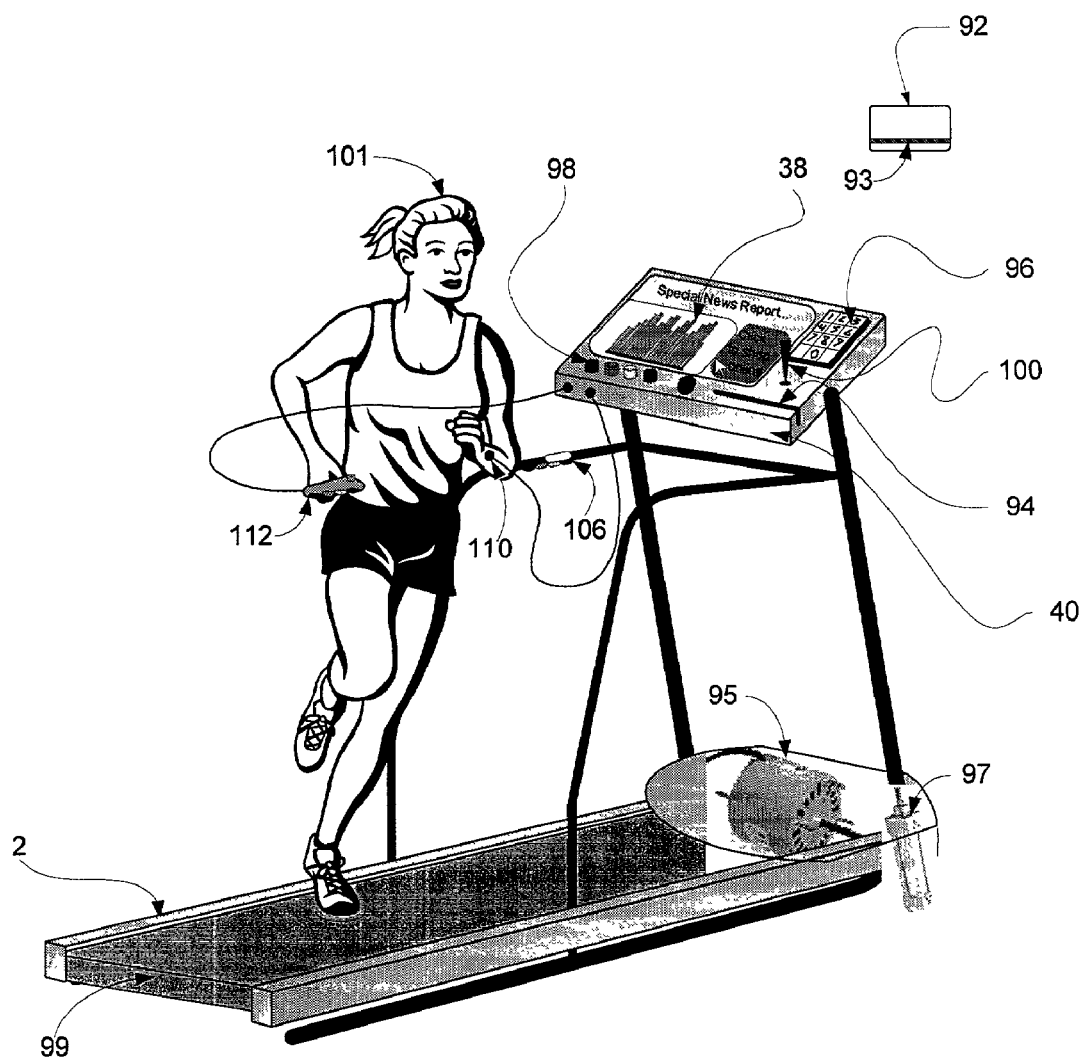
FIG. 3 shows input and output devices on a representative piece of athletic equipment, e.g., a treadmill.

FIG. 3, by way of an overview, shows a treadmill 2 equipped with a computer 40 and a viewable monitor display 38, a numeric keypad 96, a row of push buttons 98, and a joystick 100. Preferably the display on the monitor is formatted to be larger than the usual display on a comparably-sized computer screen to facilitate viewing from a greater distance while exercising. Bolding and highlighting are added features to enable this viewing.

Figure 5:
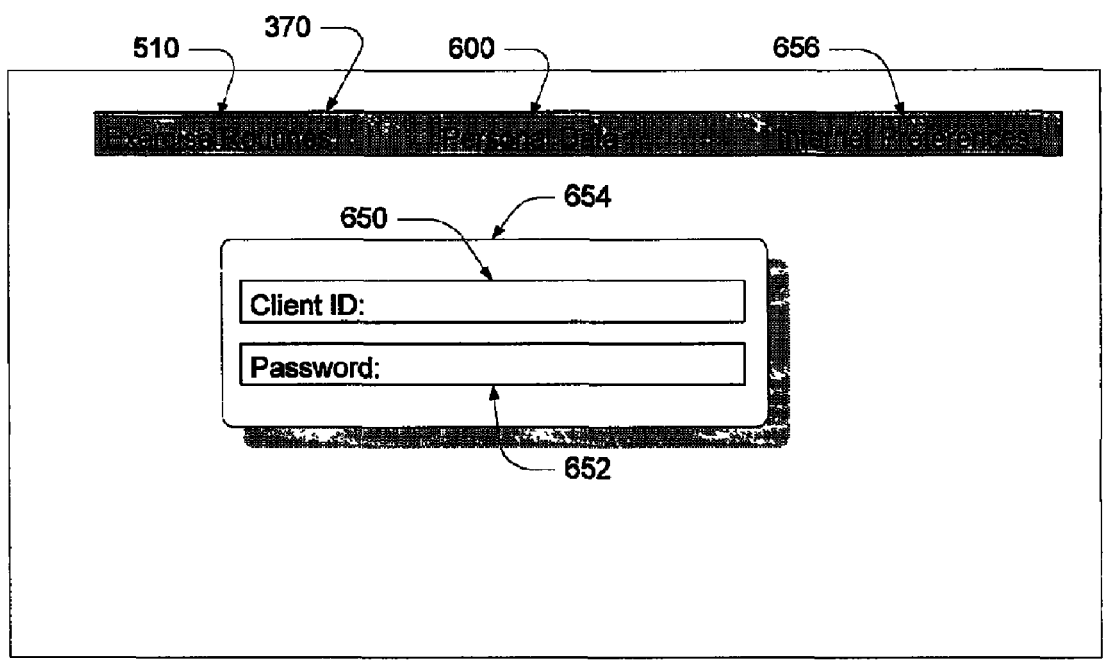
FIG. 5 is the log in screen for keeping the data secure.

FIG. 5 also shows input devices on the treadmill 2. The treadmill 2 is equipped with buttons and touch pad 106, a heart rate monitor 110, a hand held control unit 112 with buttons and a thumb operated joystick, and a magnetic strip card reader 94. The card 92 with magnetic strip 93 is swiped through the reader 94 to identify the client and to access their personalized routine. The client 101 is running on the belt 99 of the treadmill. The motor 95 drives the belt 99. The actuator 97 sets the angle of the belt 99. In a preferred embodiment, such detected information as heart rate, intensity, and speed are collected, stored, and analyzed in connection with the routine and health condition of the user, for later analysis. Signals corresponding to the heart rate, speed, and intensity can be communicated from the exercise equipment in an Internet communication for retrieving, manipulating, displaying, and storing at the user's computer.

FIG. 3 shows a treadmill 2 equipped with a viewable display monitor 38. The display monitor 38 is configured to allow a split screen display. One or more split screens may be displayed at a time. Preferably three screens are displayed during the exercise routine. One screen would show the planned exercise routine and actual results obtained, a second screen displays Internet media on topics of personal interest to the subscriber, and the third screen shows advertising preferably tailored to the profile of the subscriber. Touch screen technology could be employed as an input device.

A numeric keypad 96 is present to allow the client 101 to key in exercise parameters and identifying information to the system 1, such as a client identification number 184 and password 196. A row of push buttons 98 is used to make selections and inputs to the system. A joystick 100 is used to make selections and inputs to the system. The handrail of the treadmill 2 is equipped with buttons and touch pad 106 to make selections and inputs to the system.

In a preferred embodiment, the exercise routine is protected as private to the user, and not for open examination by a trainer or system operator. Password protection can be a minimum, but encryption such as public/private key is preferred. This is to protect those who may feel sensitive to others looking at such personal information, as well as in protecting information as charge card numbers that could be stolen. It is contemplated that some data may be shared at the discretion of the user, but most of such information will be in the nature of output from the exercise or abstract input inquiries, such as accessing a library of generic exercise routines.

A heart rate monitor 110 attached via a cable, in known manner, is present to monitor hear rate. A hand held control unit 112 with buttons and a thumb-operated joystick is present to use in making selections and inputs to the system 1.

A card reader 94 is present to allow subscriber identification to the system 1 via a magnetic strip card 92.

Figure 4:
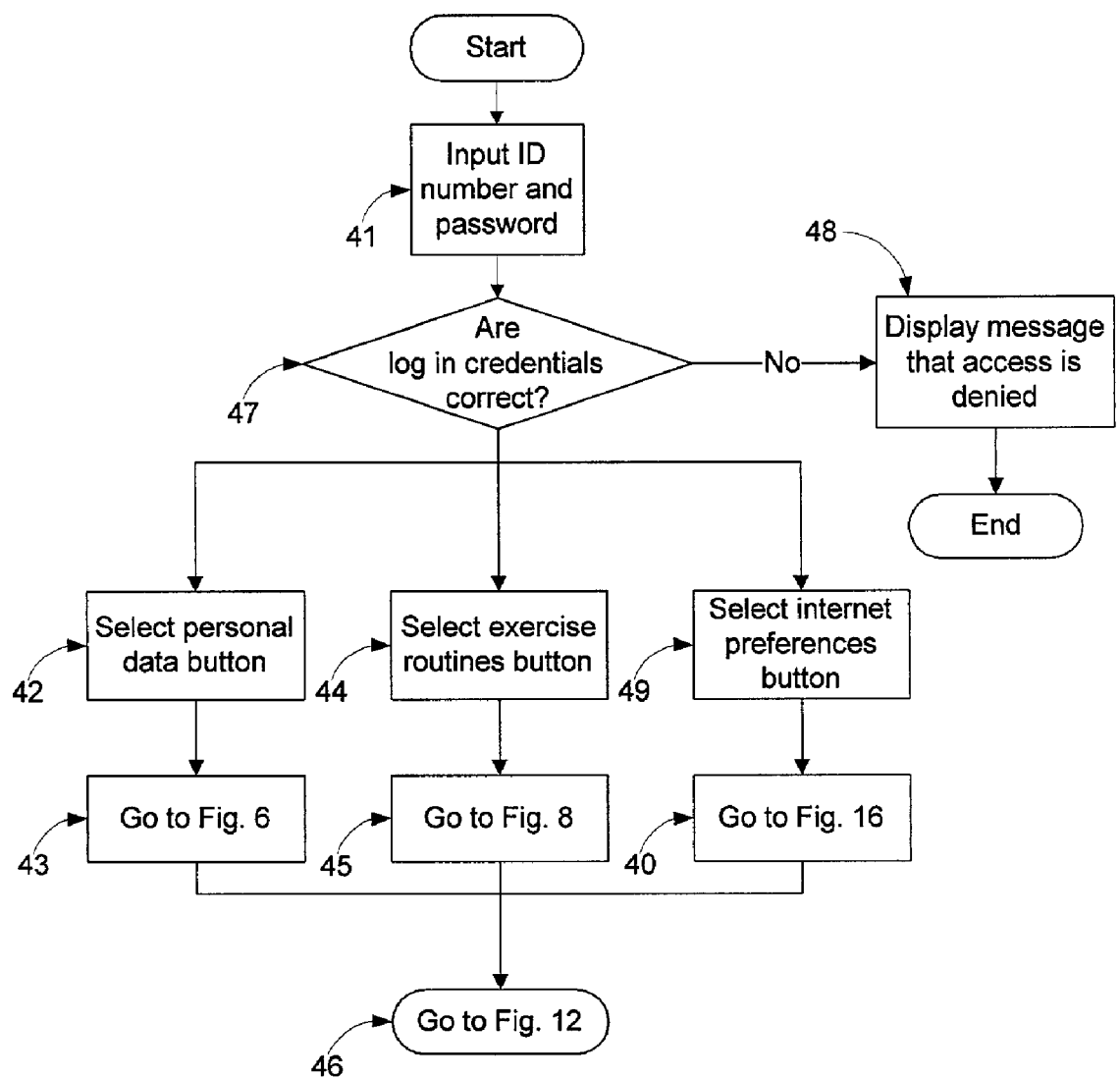
FIG. 4 is flowchart of activities of the method.

FIG. 4 represents a flowchart of activities of the present invention. In block 41 the client logs on to the system 1 by inputting the identification number and password. In block 41, the screen shown in FIG. 5 is displayed on the monitor 24 of the computer 14.

In block 47 the system 1 reads the customer table 214 to see if the identification number 184 and the password match 196. If they match then the system 1 allows the choice of going to block 42 or block 44. In block 48, if they do not match then a message is displayed that access is denied, and the system 1 is not accessible.

In block 42 the Personal Data button 600 is selected. In block 43 go to FIG. 6. In block 44 the Exercise Routines button 510 is selected. In block 45 go to FIG. 8. In block 49 the Internet preferences button 656 is selected. In block 45 go to FIG. 8. In block 46 go to FIG. 12.

FIG. 5 depicts the sign-on screen. A toolbar 370 is across the top of the screen. The toolbar 370 has the exercise routine button 510, the personal data button 600, and the Internet preferences button 656.

The window 654 has the identification number input box 650 and the password input box 652. The customer identification number 184 and the password 196 keeps the data of the client secure. The customer identification number 184 and password 196 are input in the sign-in screen. The customer identification number 184 and the identification number 650 must match the information in the customer table 214 to gain secure access to the personal settings and data. The password 184 keeps the data of the client secure. Without the correct password, no access is granted.

Figure 6:
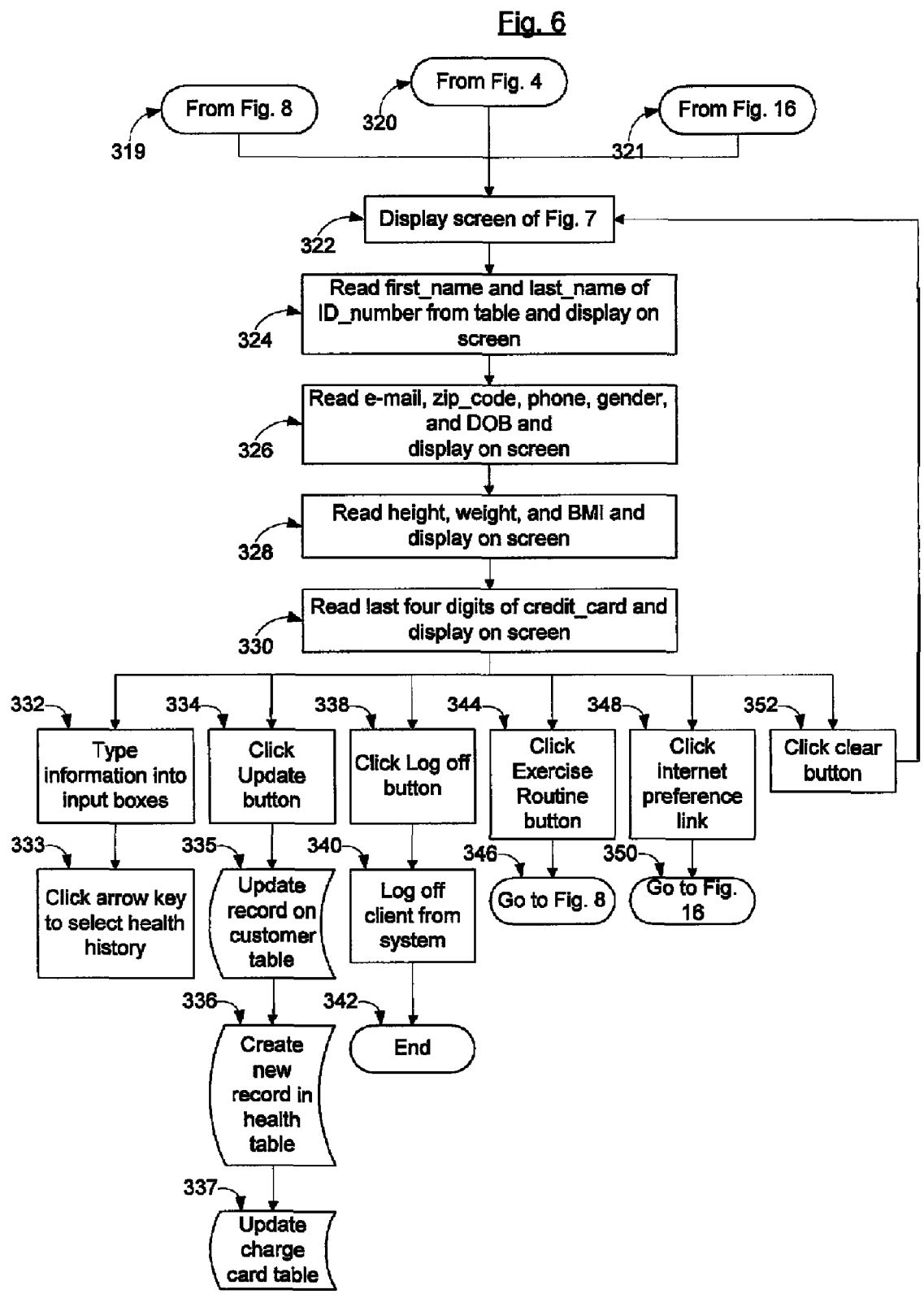
FIG. 6 is a detailed flowchart of activities to update personal information.

The personal data button 600 activates the flowchart shown in FIG. 6 upon verification of the correct identification number 184 and password 196. The exercise routine button 510 activates the flowchart shown in FIG. 8 upon verification of the correct identification number 184 and password 196. The Internet preferences button 656 activates the flowchart shown in FIG. 16 upon verification of the correct identification number 184 and password 196.

FIG. 6 represents a flowchart of activities of the present invention. Block 319 is a connector from FIG. 8. Block 320 is a connector from FIG. 4. Block 321 is a connector from FIG. 16. In block 322 the monitor 24 displays the screen from FIG. 7. In block 324 read the first name and last name from the customer table 214 that corresponds to the identification number input in block 41, and display this information on the screen. In block 326 read the e-mail address, zip code, telephone number, gender, and date of birth from the customer table 214 that corresponds to the identification number input in block 41, and display this information on the screen. In block 328 read the height, weight, and body mass index from the customer table 214 that corresponds to the identification number input in block 41, and display this information on the screen. In block 330 read the last four digits of the credit card number from the customer table 214 that corresponds to the identification number input in block 41, and display this information on the screen.

In block 332 types information into the input boxes 608, 610, 620, 624, 628, 612, 622, 626, 614, 618, 616, and 630. If the input boxes were blank from the operations in blocks 326, 328, or 330, then the information will simply fill the field, if the boxes had information then the data typed will replace the other data. In block 333 make a selection by clicking the down arrow button 648 and the list 226 will appear as a drop down menu.

In block 334 click the Update button 632. In block 335 the record will be updated on the customer table 214 in the row that corresponds to the identification number input in block 41 by writing the data from the e-mail 608, zip cope 610, phone 620, sex 624, and date of birth 262 input boxes. In block 336 an additional record will be created on the health table 216 that corresponds to the identification number input in block 41 by writing the data from the health history input box 614 and the date input box 618. In block 337 update the credit card data and expiration date on the customer table 214 if there are sixteen digits in the credit card input box 616.

In block 338 click the log off button 603. In block 340 log the client off of the system 1. In block 342 the flowchart ends.

In block 344 click the exercise routine button 510. In block 346 go to FIG. 8.

In block 348 click the Internet preference button 656. In block 350 go to FIG. 16.

In block 352 click the clear button 602 and go to block 322 and repeat the steps in blocks 324, 326, 328, and 330. The tables 214, 216, and 218 are not updated, any changes will be lost.

Figure 7:
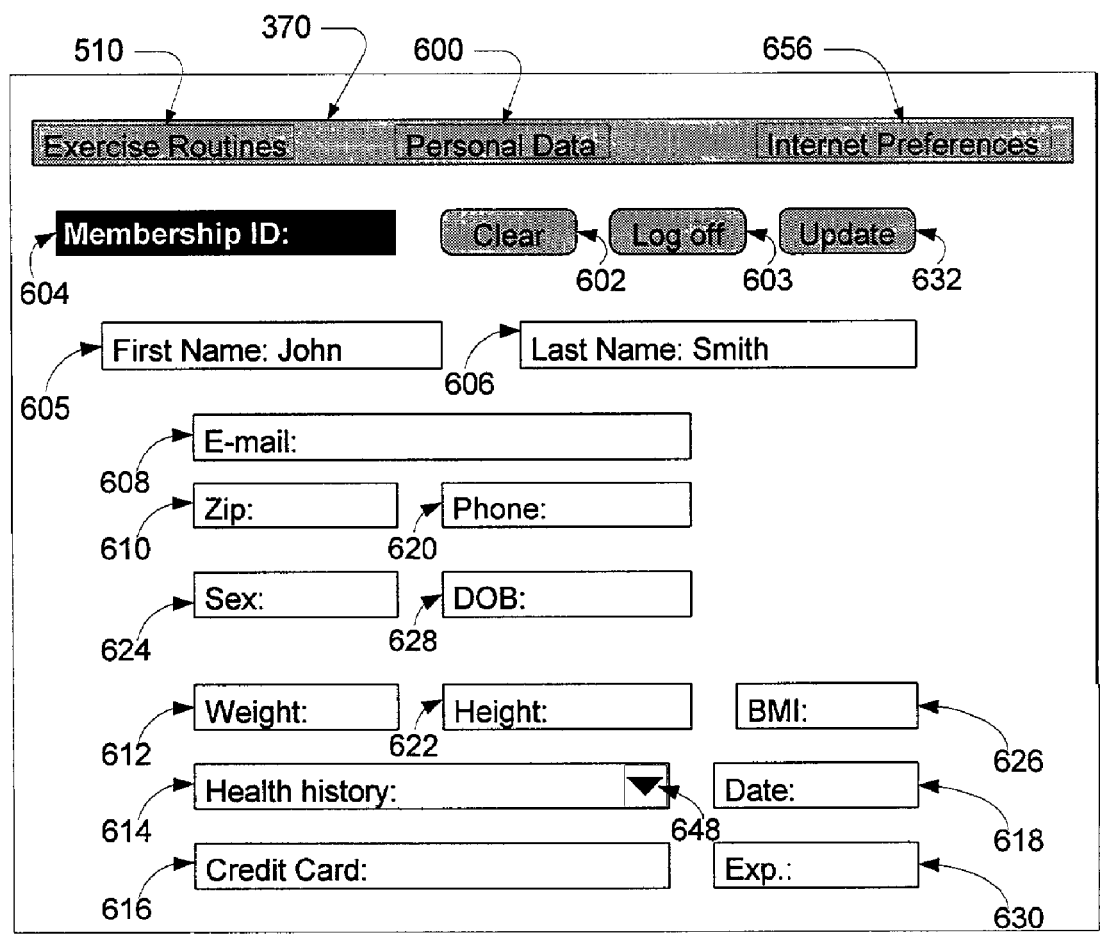
FIG. 7 shows a personalized interface screen that a subscriber to the system has access to when logged via a personal computer.

FIG. 7 depicts the personal data screen. A toolbar 370 is across the top of the screen. The toolbar 370 has the exercise routine button 510, the personal data button 600, and the Internet preferences button 656.

Below the toolbar 370 is displayed the identification number 604 of the client, the clear button 602, the log off button 603, and the update button 632. Below the identification number 604 is displayed the first name 605 and last name 606 of the client.

Below the names is the e-mail input box 608, the zip code input box 610, the telephone number input box 620, the gender input box 624, the date of birth input box 628. Next is the weight input box 612, the height input box 622, and the body mass index input box 626. Below that is the health history drop down menu box 614, with the arrow key 648. Next to it is the date input box 618. Below is the credit card input box 616 and the expiration date input box 630.

The personal data button 600 activates the flowchart shown in FIG. 6 upon verification of the correct identification number 184 and password 196. The exercise routine button 510 activates the flowchart shown in FIG. 8 upon verification of the correct identification number 184 and password 196. The Internet preferences button 656 activates the flowchart shown in FIG. 16 upon verification of the correct identification number 184 and password 196.

Figure 8:
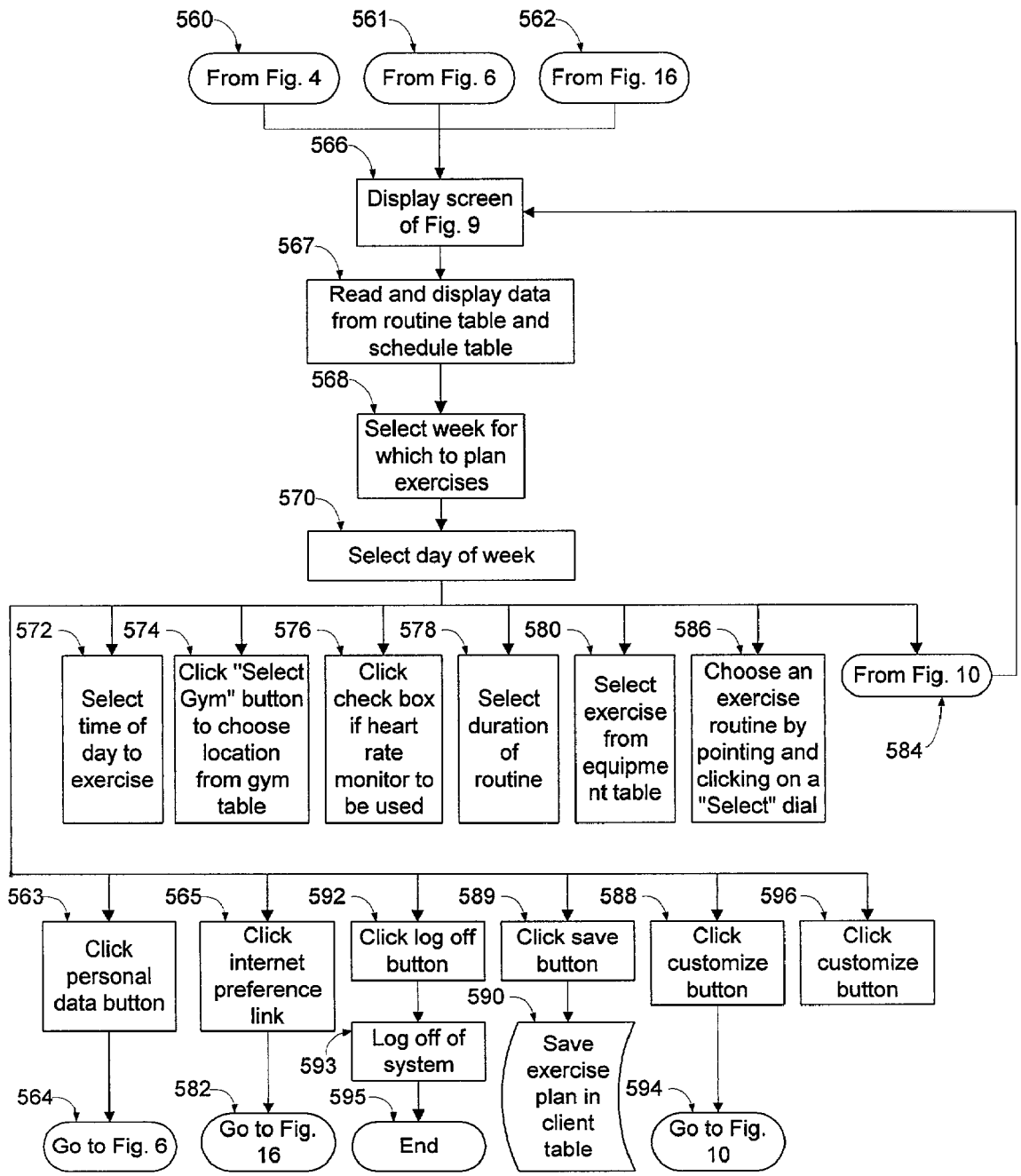
FIG. 8 is a detailed flowchart of activities to plan a personalized exercise schedule.

FIG. 8 represents a flowchart of activities of the present invention for planning exercise sessions. Block 560 is a connector from FIG. 4. Block 561 is a connector from FIG. 6. Block 562 is a connector from FIG. 16. Block 584 is a connector from FIG. 10.

Figure 9:
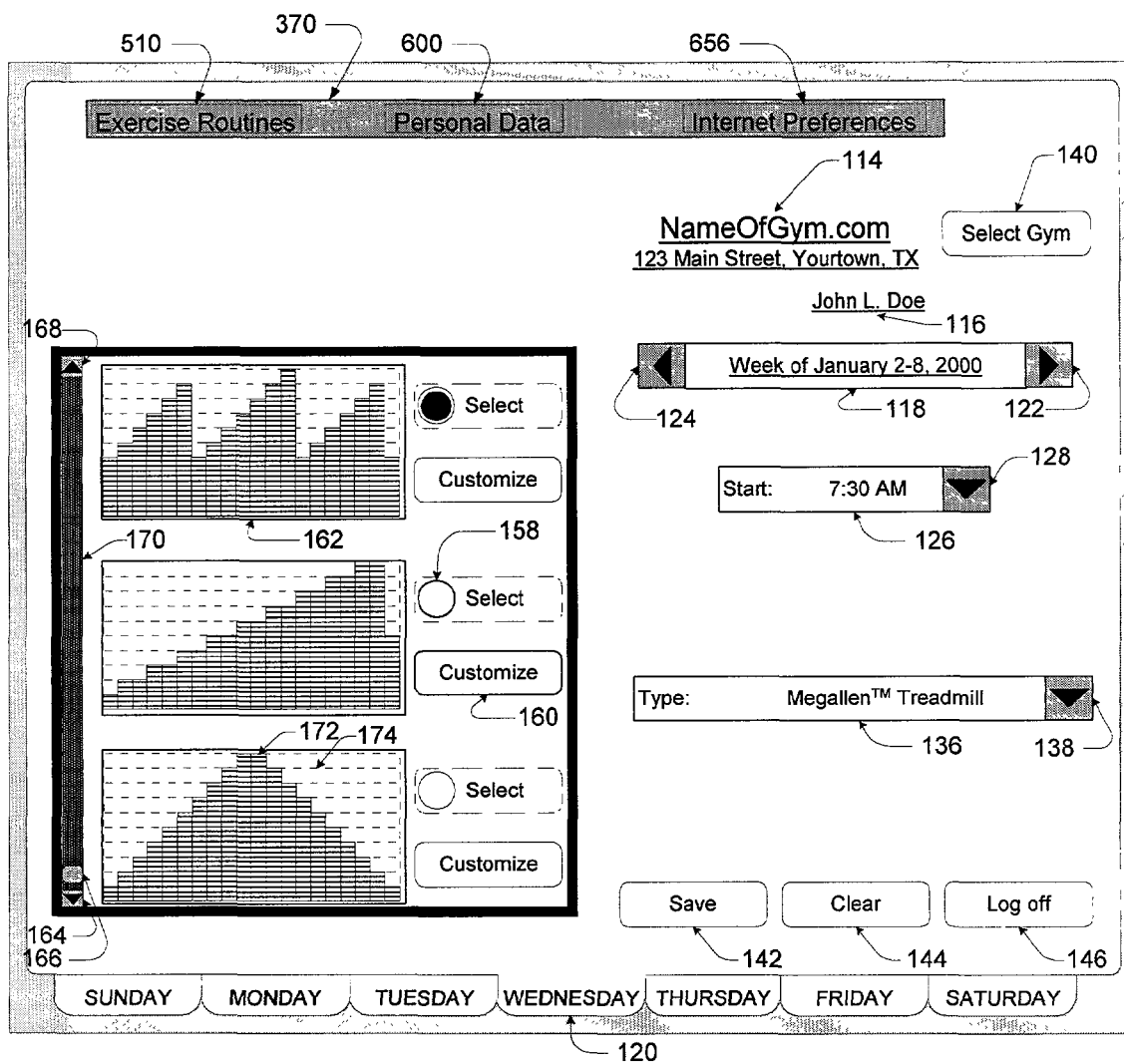
FIG. 9 shows an interface screen to plan a personalized exercise schedule.

Block 566 displays the screen of FIG. 9. In block 568 select the week for which to plan exercises by clicking on the left arrow 124 or right arrow 122 buttons. In block 570 select the day of the week by clicking on a day tab 120.

In block 572 select the time of the day to exercise by inputting a time in the planned start time input box 126. In block 574 click on the select gym button 140 and a pop up list will display a list of gyms from the gym table 260. Make a selection and it will be displayed 114 on the screen.

In block 576 click the check box 148 if a heart rate monitor is to be used. In block 578 select the duration of the exercise routine by inputting a number in the duration input box 130. In block 580 select the type exercise equipment to be used from the exercise input box 136.

In block 586 choose an exercise routine by clicking on a select dial 158. In block 588 click the customize button 160 to modify that exercise routine. In block 594 go to FIG. 10.

In block 590 click the save button 142 and the data is saved in the schedule 310 for the identification number 184 and the routine table 298 for the routine identification number 294.

In block 592 click the log off button 146. In block 593 log the client off of the system 1. In block 595 the flowchart ends.

In block 563 click the personal data button 600. In block 564 go to FIG. 6.

In block 565 click the Internet preference button 656. In block 582 go to FIG. 16.

In block 596 click the clear button 144 and go to block 566 and repeat the steps in blocks 567, 568, and 570. The tables 298 and 310 are not updated, any changes will be lost.

FIG. 9 shows the screen used to make a personalized exercise schedule. A toolbar 370 is across the top of the screen. The toolbar 370 has the exercise routine button 510, the personal data button 600, and the Internet preferences button 656.

The name of a gym and address 114 appears in the upper right hand corner of the screen. This is the name of the gym in which the fitness equipment is physical located. The name is a hyperlink to the home web site of the gym. Next to the name is a "Select Gym" button 140. The client may click on this button to see a list of other gym locations, as 260 of FIG. 14. By clicking on another selection from that list, the client may select another location to perform their exercise routine.

Below the name of the gym 114 is the name of the client 116. This is a hyperlink to the personal records of the subscriber. By clicking on this link 116 the subscriber has access to personal information and records, as in FIG. 16.

Below the name of the subscriber is the week 118 for which the subscriber is planning exercise routines. The days of the week are listed at the bottom of the screen on the tabs 120. The arrows to each side of the date box 118 are used to view the next week, by clicking the right arrow button 122, or the previous week, by clicking the left arrow button 124. The date 118 is a hyperlink to the calendar function of the personal information manager of the client or gym.

Below the date 118 is the planned start time 126 for the exercise routine. This is a dropdown menu selection. By clicking on the arrow 128, the user may select another time for exercising.

Below the planned start time 126 is the input box to select the type of exercise equipment 136 to be used. This is a dropdown menu listing the equipment of the gym 114 that is named at the top of this screen. By clicking on the arrow button 138, a complete list, 296 on FIG. 14, of available equipment at that gym 114 will be listed. The client will click on the type equipment for which they will exercise.

The save button 142 will save the changes made by the client. The clear button 144 will clear all changes made by the client. The Log off button 146 will log off the client from the system 1 after saving the changes made by the client.

The left side of the screen displays the profile 162 of the planned exercise session. In the illustrated embodiment, the height of each column 172 on a graph represents the speed at which the treadmill belt is traveling while the width of each column 172 represents a time interval. The subscriber may choose one of a few exercise profiles shown, or they may use the scroll button 166 on the scroll bar 170, to view other intensity profiles. The customize button 160 allows the subscriber to modify the session profile 162. By clicking on the up arrow button 166 the exercise profiles 162 will scroll up to show additional exercise routines. By clicking on the down arrow button 164 the exercise profiles 162 will scroll down to show additional exercise routines. By clicking on the "Select" circle 158 the exercise profile adjacent to that button will be as the designated exercise routine.

Note that in forming the profile, a charge card and authorization for use of the card can be stored. The authorization may include renewal of membership, online or other purchases, etc. Such a profile can be useful in carrying out an on line purchase using the exercise machine while exercising, e.g., by using the specially adapted exercise machine discussed herein.

The profile is a versatile tool. It can, depending on the embodiment, control media presented to the user while on the exercise machine, for example, video, TV, electronic magazines, shopping sites, e-mail, stock prices and business information, news reports, and even entertainment such as horoscopes, hobby information, etc. Multimedia can be enabled or controlled by the profile, with a speaker jack for headphones mounted on the exercise equipment. As discussed elsewhere herein, a joystick, touch screen, touch pad sensors on the equipment, or programmed surfing can also be carried out with the present invention. The profile is also used in setting a filter for web subject matter and content to avoid not displaying sensitive or confidential information. Additionally, the profile can store limited permission (or tokens) to enable forming groups of users, say by ability or desired exercise activities, or other partial but not complete access to data in the profile. Such limited access can also be utilized by the athletic facility, for example, in charging to a charge card number without having access to information the user deems personal.

Figure 10:
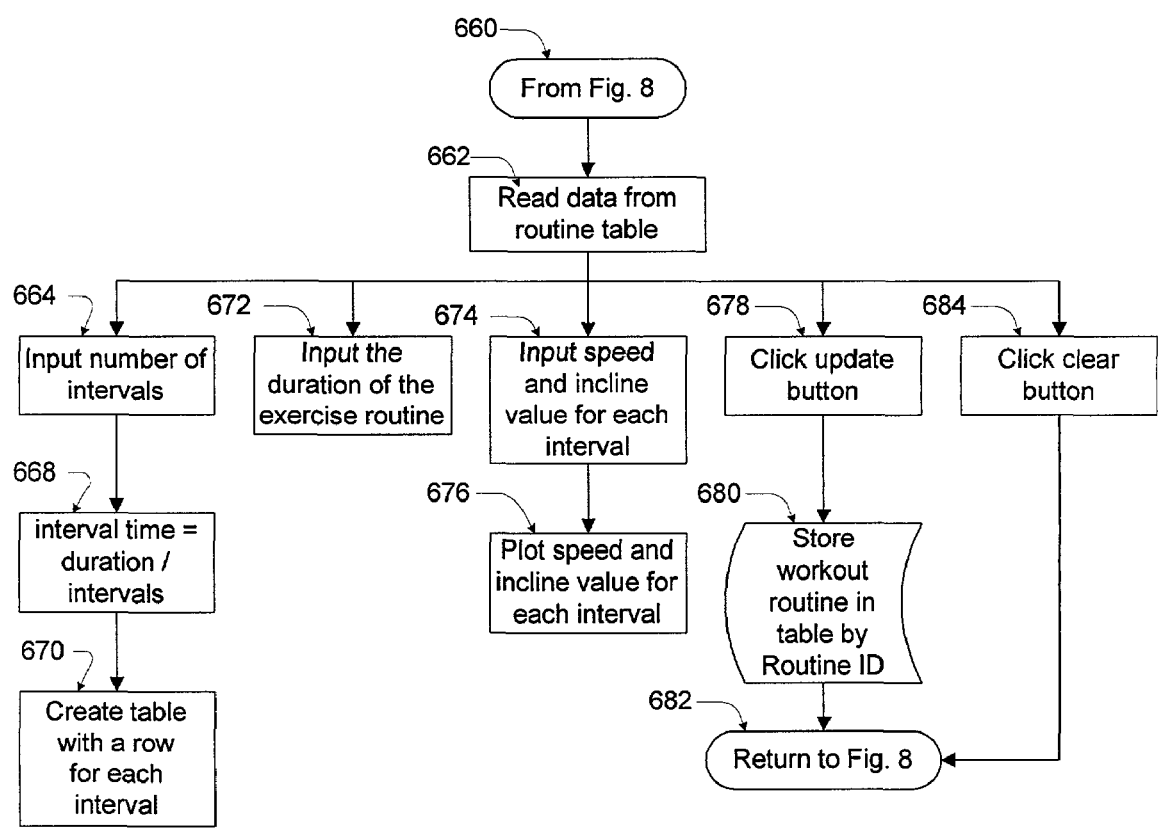
FIG. 10 is a flowchart of activities to modify an exercise routine.

FIG. 10 represents a flowchart of activities of the present invention for modifying an exercise routine. Block 660 is a connector from FIG. 8. Block 662 reads the data from the routine table 298. In block 664 input the number of intervals in the intervals input box 518. Block 668 calculates interval time to equal the duration divided by the number of intervals. In block 670 create a row for each interval in the routine table 298.

In block 672 input the duration of the exercise routine in the duration input box 134. In block 674 input the speed for each interval in the speed column 526, and input the incline level for each interval in the incline column 528. Block 676 plots the exercise routine in the graph 520.

In block 678 click the update button 532. Block 680 stores the exercise routine in a routine table 298. In block 684 click the clear button 534. Block 682 returns to block 584 of the flowchart in FIG. 8.

Figure 11:
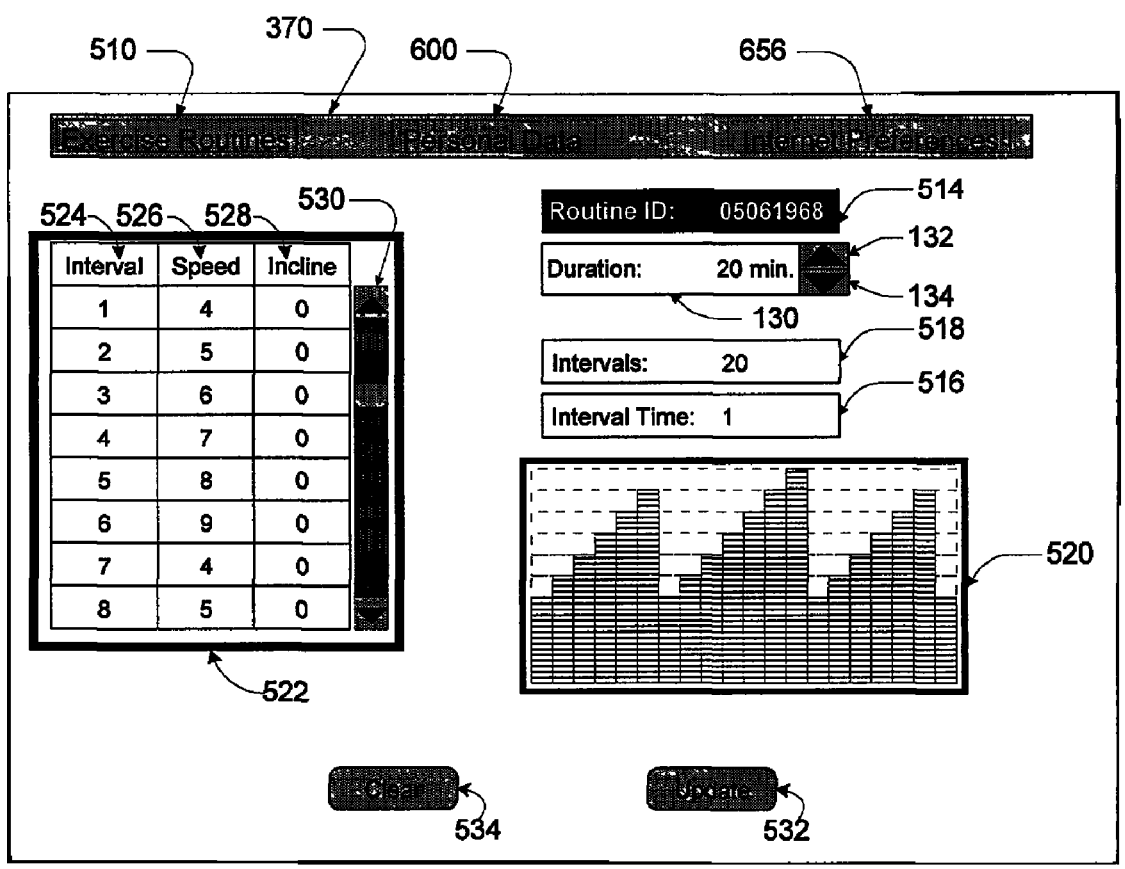
FIG. 11 shows an interface screen to modify an exercise routine.

FIG. 11 shows the screen used to modify an exercise routine. A toolbar 370 is across the top of the screen. The toolbar 370 has the exercise routine button 510, the personal data button 600, and the Internet preferences button 656.

The input matrix 522 is on the left side of the screen. The matrix 522 has an interval column 524, a speed column 526, and an incline column 528. A scroll bar 530 is on the left of the matrix for navigating up and down the rows.

In the upper left is the routine identification display 514.

Below the display 514 is an input box for the duration 130 of the exercise routine. By clicking on the up arrow 132, the duration will increase. By clicking on the down arrow button 134, the duration will decrease.

Below the duration 130 is the interval input box 518. Below that input box is the interval time input box 516. A graph 520 of the exercise routine is in the lower right corner of the display.

Across the bottom of the screen is the clear button 534, and the update button 532.

Figure 12:
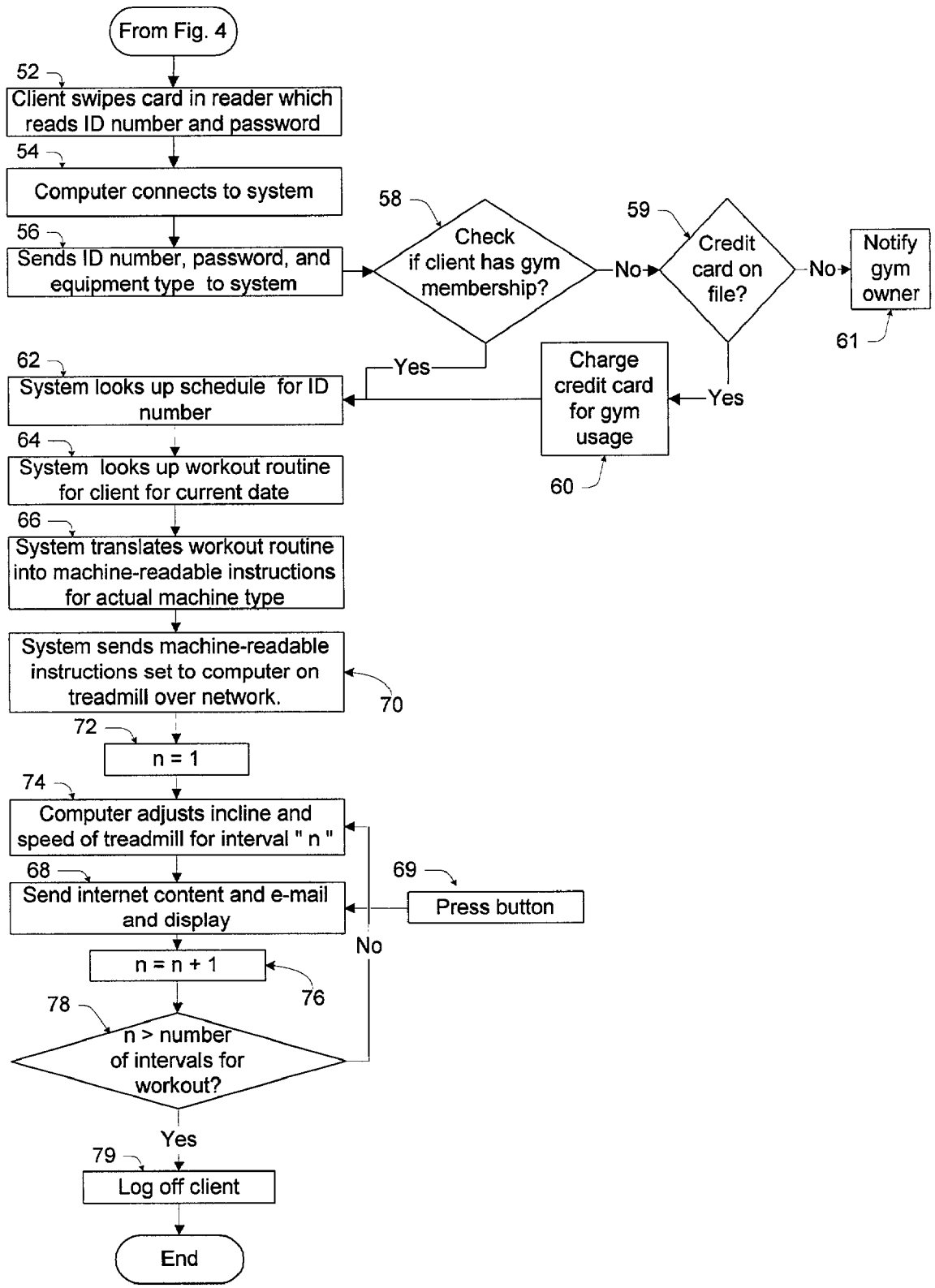
FIG. 12 is a flowchart of activities describing how the client would use the invention in performing their exercise routine.

FIG. 12 is a schematic representation of the client performing their exercise routine, which is secured by a password. In block 52 the client swipes an identification badge 92 through the card reader 94. The card 92 has a magnetic strip 93. In block 54 the computer 40 on the treadmill 2 connects to the host computer 10. In block 56, the computer 40 sends identification number and password to host computer 10. In block 58, the host computer 10 checks if client has a gym membership. If no, then in block 59 the host computer 10 checks to see if the client has a credit card on file. If the client does not have a credit card on file, then the application ends.

If in block 59 the answer is yes, then the host computer charges the credit card a usage fee for the gym, and then go to block 62. If in block 58 the answer was yes, then go to block 62.

In block 62 the host computer looks up the schedule for the client based upon the identification number. In block 64 the host system 1 looks up the exercise for the client on the schedule for the current date.

In block 68 the system 1 translates the exercise routine into machine-readable instructions for the actual machine type.

In block 70, the host system 1 sends a machine-readable instruction set to the computer 40 over the network.

In block 72, the variable n=1. The variable n counts the number of intervals of the exercise routine. In block 74, the treadmill 2 performs the instruction set for interval n=1.

In block 68 the host system 1 sends Internet content and e-mail to the computer 40 over the network. In block 69 the client 101 can press a button 112 to trigger the system 1 to send Internet material or e-mail.

In block 76, the interval counter is incremented by 1 by the computer 1. In block 78, the computer 10 checks to see if the number of intervals is greater than the number of intervals for the exercise routine. If no, then the computer goes to block 74 and performs the instruction set for the next value of n. If the response for block 78 is yes, then the computer goes to block 79 and logs off the client, and the program ends.

Figure 13:
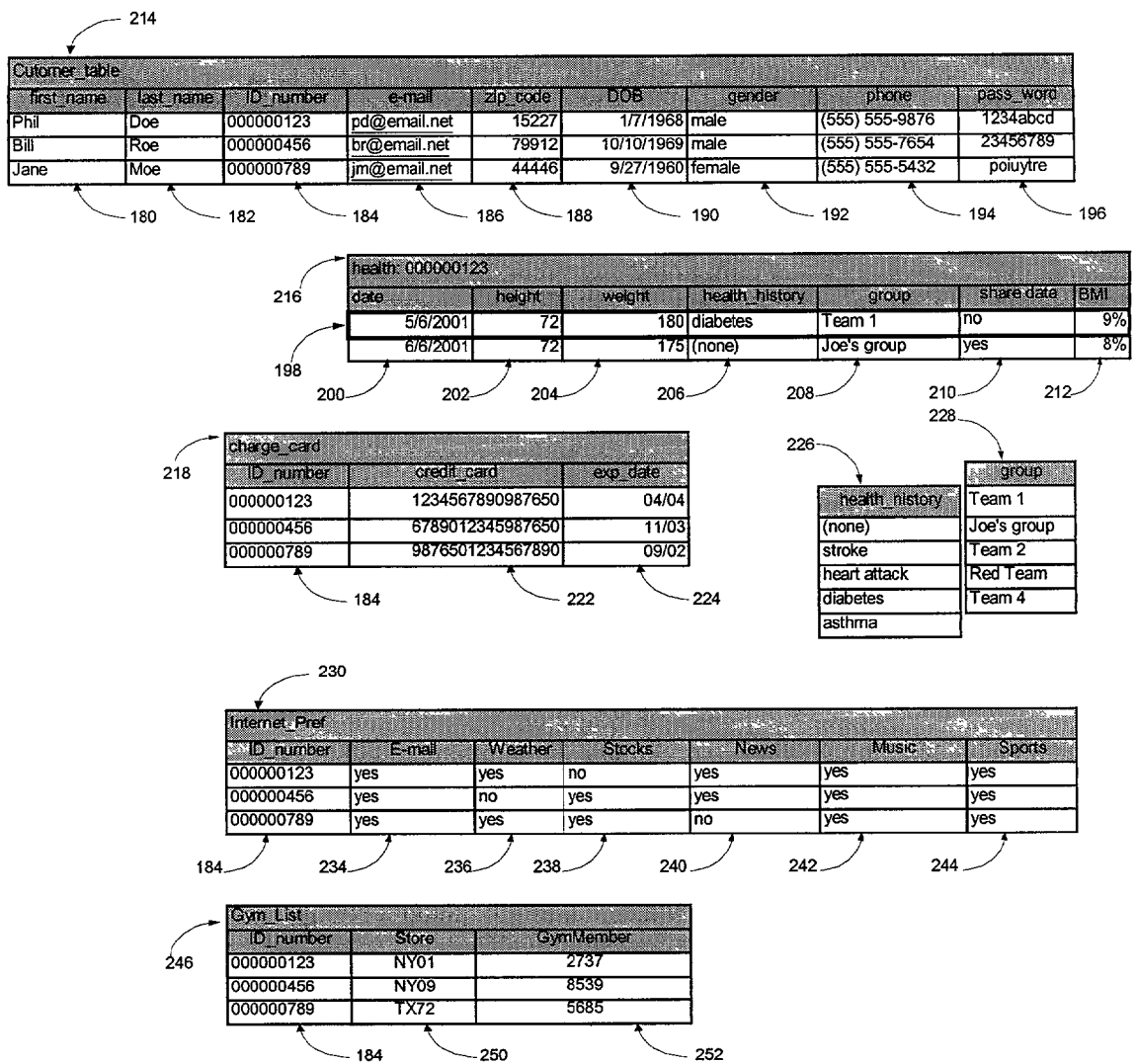
FIG. 13 depicts the tables that are part of this invention for managing the data of the clients.

FIG. 13 depicts the tables that are part of this invention for managing the data of the clients. The customer list 214 is a table of information on each customer. The customer list 214 has a field for the first name 180 and last name 182 of the customer. The first name 180 field is an alpha field, 12 characters wide. The last name 182 field is an alpha field, 20 characters wide.

Each customer is assigned an identification number 184; this is a numeric field, 9 characters wide. The identification number 184 is the key field which links the customer list table 214, to the health and group table 216, to the charge card table 218, to the Internet preference table 230, and to the gym list table 246.

The customer list table 214 also contains the e-mail address 186 of the customer, their zip code 188, date of birth 190, gender 192, telephone number 194, and password 196.

The customer identification number 184 and the password 196 keeps the data of the client secure. The customer identification number 184 and password 196 are input in the sign-in screen of FIG. 17. The customer identification number 184 is input into the "Client ID" input box 650, the password 196 is input into the "password" input box 652 by the customer to gain secure access of their personal settings and data. The password 184 keeps the data of the client secure. Without the correct password, no access is granted. The customer identification number 184 and the password 196 are also written on the magnetic strip 93 of the identification badge 92.

A health table 216, with identification number 184, is created for each client. A record with the date 200, health history 206, weight 204, height 202, and body mass index 212, is created each time the "Update" button 632 is pressed. Health records are not deleted from the table 216; additional records are added. A health list 226 is a list that contains various health conditions. By clicking on the down arrow button 648 of FIG. 16, the list will drop down for the client to make a selection.

Clients may input credit card information so that purchase may be charged against the account. Charge card information is stored in the charge card table 218. The credit card number 222, and the expiration date 224 are stored with the identification number 184 of the client.

Clients may input their preferences for Internet media which is displayed during the exercise session. Internet preference information is stored in the Internet preference table 230. Their preference for e-mail 234, weather 236, stocks 238, news 240, music 242, and sports 244 are stored with the identification number 184 of the client.

Clients select the gym for which they are members. The identification number 250 and gym membership number 252 are stored with the identification number 184 of the client on the gym list table.

FIG. 14 displays the tables for managing the data of the gyms and equipment. This table 280 is filled in by using the display screen in FIG. 12. The gym table 260 has a filed for the gym name 262, a gym identification number 250, an e-mail address 266, a street address 268, the city 272, the state 274, the zip code 276, and the telephone number 278 for each gym.

For each gym an inventory table 280, with the gym identification number 250, is created. The gym identification number 250 is a key field linking the tables. The inventory table 280 is a listing of the exercise equipment of that particular gym. Each piece of gym equipment has an equipment identification number 284. There are fields to capture the brand 286, type 288, serial number 290, and model 292 of each piece of exercise equipment.

The type list 296 is a list of the various types of exercise equipment. The type list appears when the "Search" button 452 is pressed from FIG. 12. By pointing and clicking on an item on the list 296, the type field 288 is populated in the inventory table 280.

Each exercise routine is created and stored in a routine table 298, each with an identification number 294. The table 298 has a column for the interval 300, the duration 302, the speed 304, the incline 306, and the heart rate 308. A schedule table 310 is created for each client and the client identification number 184 is assigned. The table has the date 312 of the planned exercise activity, the exercise type 314, and the brand 270 and model 316 of the exercise equipment. The table has a column for the routine number 270. The routine number 294 is a key field that links the routine table 298 to the schedule 310.

FIG. 15 shows an interface screen to update Internet preferences. A toolbar 370 is across the top of the screen. The toolbar 370 has the exercise routine button 510, the personal data button 600, and the Internet preferences button 656. A membership identification number display 604 is below the toolbar 370 on the left side of the screen. Next to the display 604 is the clear button 602, the log off button 603, and the update button 632.

Below the display 604 is the "Check Internet preferences" title 634. Below the title 634 are check boxes to select Internet media. There is the e-mail check box 636, the news check box 638, the weather check box 640, the sports check box 642, the stocks check box 644, and the music check box 646.

FIG. 16 a flowchart of activities describing how to update Internet preferences. Block 470 is a connector from FIG. 4. Block 472 is a connector from FIG. 8. Block 474 is a connector from FIG. 16. Block 476 displays the screen of FIG. 15. Block 478 reads data from the Internet preference table. In block 480 click on a check box to select the type of Internet media. In block 482 click on the update button 632. Block 484 updates the Internet preference table 230.

In block 486 click the log off button 603. Block 488 logs the client off of the system 1. Block 502 ends the flowchart activities.

In block 492 click the exercise routines button 510. Go to FIG. 8 in block 494.

In block 496 click the personal data button 600. Go to FIG. 6 in block 496.

In block 500 click the clear button 602 and go to block 476. Any modifications made will not be saved.

While the above description contains many specificities, these should not be construed as limitations on the scope of the invention, but rather as an exemplification of one preferred embodiment thereof. Many other variations are possible such as, but not limited to, those described in the Objects and Advantages section above. Thus, the scope of the invention should be determined by the appended claims and their legal equivalents, rather than by the principal embodiment and other examples described above.

I claim:

1. An apparatus to produce an exercise routine personalized by a user, the apparatus including:
   a first computer system programmed so as to facilitate forming machine-readable instructions corresponding to a personalized exercise routine, wherein said machine-readable instructions are protected as private to the user;
   a portable memory device storing the personalized exercise routine formed in the machine-readable instructions and received from the first computer system; and
   a second computer system programmed to carry out operations comprising user-triggered enabling of:
      translating the private personalized exercise routine, stored in the portable memory device and retrieved from the portable memory device, to a different personalized private exercise routine for each different type of user-selected exercise machine,
   controlling an exercise machine in carrying out the different personalized private exercise routine.

2. The apparatus of claim 1, wherein the operations include storing, in a personal account, medical information and a charge card number respectively corresponding to the user, wherein said account is maintained as personal to the user.

3. The apparatus of claim 1, wherein the operations include forming a profile of the user; and
   maintaining the profile of the user as personal to the user.

4. The apparatus of claim 1, the first computer system is programmed so as to facilitate:
   downloading and storing the exercise routine on the portable memory device that is physically transportable to said exercise machine to enable said user-triggered engaging step.

5. The apparatus of claim 4, wherein said storing includes storing by making an addition to a library of routines.

6. The apparatus of claim 3, wherein the operations include storing, in said profile, a charge card number associated with the user.

7. The apparatus of claim 6, wherein the operations include enabling, with the stored charge card number, carrying out an on line purchase from the different type of exercise machine while exercising.

8. The apparatus of claim 3, wherein the operations include providing a control for at least one type of media including video, TV, e-mail, stock prices, news, horoscope, hobby information, Internet media, or an electronic magazine, the control being stored in a profile of the user.

9. The apparatus of claim 8, wherein the providing a control is carried out with two of the media.

10. The apparatus of claim 8, wherein the providing a control is carried out with three of the media.

11. The apparatus of claim 10, wherein the operations include implementing the control by displaying media at said different type of exercise machine.

12. The apparatus of claim 3, wherein the operations include controlling with said profile to output to a display device and to a speaker jack at the exercise machine.

13. The apparatus of claim 1, wherein the operations include accepting a gym registration application over a network.

14. The apparatus of claim 3, wherein the operations include managing gym membership, with said second computer system, including tracking fees of gym users and issuing invoices.

15. An apparatus to create a personalized exercise routine, the apparatus including:
 a first computer system programmed so as to provide at least one user interface that allows a user to select a type of exercise machine, and to create a private personalized exercise routine for a type of exercise machine that is selected;
 a second computer system programmed so as to carry out operations including translating the private personalized exercise routine, stored in and retrieved from a portable memory device, to a different personalized private exercise routine for each different type of user-selected exercise machine; and
 wherein said second computer system is comprised of at least one of the types of exercise machine that carries out one said different exercise routine.

16. The apparatus of claim 15, wherein the operations include
 allowing a user profile to be formed and stored in a personal account that is maintained as personal to the user.

17. The apparatus of claim 15, wherein the exercise routine comprises
 a cardiovascular routine; and wherein
 signals corresponding to the exercise routine are communicated over a network to the different type of exercise machine.

18. The apparatus of claim 15, wherein said operations includes:
 allowing access, via a virtual private network, to a web-accessible library of modifiable preprogrammed routines; and
 allowing modification of said preprogrammed routines.

19. The apparatus of claim 15, wherein the first computer system is programmed so as to facilitate:
 selecting a type of cardiovascular fitness machine as the different type of exercise machine, and specifying a duration of an exercise, a number of time intervals, an intensity, and a speed for each of the intervals.

20. The apparatus of claim 15, further including wherein the operations include facilitating
 swiping at least one of a credit card or smart card for access to the different type of exercise machine.

21. The apparatus of claim 20, wherein said swiping is carried out with a card reader on a reception admission control system.

22. The apparatus of claim 15, wherein the operations include
 providing to the first computer system, via communication over a network, an agreement to abide by gym rules.

23. The apparatus of claim 15, wherein the operations include providing user access to the Internet at the exercise machine that carries out the one said different exercise routine.

24. The apparatus of claim 15, further including an interface for communicating at least some personal profile data between computer systems of different gyms.

25. The apparatus of claim 15, wherein the first computer system is programmed so as to facilitate forming a set of exercise routines translated to control different types of exercise machine, and storing the set in the portable memory device.

26. The apparatus of claim 17, further including a browser interface presented at said exercise machine to control Internet communication.

27. The apparatus of claim 15, further including a browser interface presented at said different type of exercise machine to control Internet communication.

28. The apparatus of claim 26, further including an interface for communicating the exercise routine to a controller between the Internet and the exercise machine.

29. The apparatus of claim 27, further including an interface for communicating the exercise routine to a controller between the Internet and the different type of exercise machine.

30. The apparatus of claim 16, wherein the operations include controlling, with said profile, interaction with Internet communication while exercising by use of a device that is at least one of a video game joystick on said different type of exercise machine or a flexible touch pad on at least one handle of the different type of exercise machine.

31. The apparatus of claim 16, wherein the operations include controlling with said profile programmed, hands-free, Internet communication.

32. The apparatus of claim 31, wherein said controlling includes controlling selectable content and presentation format coordinated with timing of the exercise routine.

33. The apparatus of claim 16, further including a sensor monitoring heart rate at the different type of exercise machine, and wherein the operations include storing said heart rate in said user profile.

34. The apparatus of claim 33, wherein the operations include: monitoring speed and intensity of the exercise routine; and
 storing said speed and said intensity in said user profile.

35. The apparatus of claim 34, further including an interface for communicating signals corresponding to said heart rate, said speed, and said intensity in an Internet communication sent to the user of the first computer system.

36. The apparatus of claim 15, wherein the first computer system is programmed to facilitate utilizing a calendar function to schedule use of the different type of exercise machine.

37. The apparatus of claim 15, wherein the first computer system is programmed so as to facilitate utilizing a calendar function to schedule use of a group of pieces of exercise machine.

38. The apparatus of claim 15, further including a virtual private network providing at least one user interface from the second computer system to the first computer system.

39. The apparatus of claim 15, wherein the operations include formatting output at a display device at said different type of exercise machine, said formatting including selectable enlarging of the output.

40. The apparatus of claim 16, further including an interface enabling Internet navigation at said different type of exercise machine during exercising.

41. The apparatus of claim 16, wherein the operations include:
permitting, at direction of the user, access to an exercise report, and storing the report in the profile.

42. The apparatus of claim 16, wherein the different type of exercise machine comprises one of at least a treadmill, an elliptical trainer, a stationary bike, a stationary ski machine, a stationary rowing machine, or a resistance type machine.

43. The apparatus of claim 16, wherein the first computer system is programmed so as to facilitate digitally specifying a location of the different type of exercise machine so that exercising is carried out at a location corresponding to at least one of a home, a home gym, a spa, an exercise facility of an apartment complex, and a hotel.

44. The apparatus of claim 16, wherein the operations include maintaining a business operations database used in carrying out the translating.

45. The apparatus of claim 16, wherein the operations include forming a client profile database containing a profile for each of a plurality of users.

46. The apparatus of claim 16, wherein the operations include controlling output of visual and audio Internet media with said profile, the media including at least one of music, a video, multimedia, or chat.

47. The apparatus of claim 16, wherein the first computer system is programmed so as to facilitate optionally viewing and configuring reports including intensity levels of the exercise routine and heart rate through a web browser interface.

48. The apparatus of claim 16, wherein the operations include providing, at the different type of exercise equipment, at least one user interface that includes a corresponding media display, the media from the group including at least one of video, audio, and text.

49. The apparatus of claim 16, wherein the operations include providing data to a resource pool database of available exercise machines.

50. The apparatus of claim 16, wherein the operations include enabling the user:
logging on to the second computer system by inputting an identification number and password.

51. The apparatus of claim 16, wherein the operations include facilitating input into said profile of the user's birth date, gender, weight, height, or health history.

52. The apparatus of claim 50, wherein the operations include facilitating input of membership of a gym into said profile.

53. The apparatus of claim 52, wherein the operations include communicating location of the gym and a gym membership identification number to the first computer system.

54. The apparatus of claim 16, wherein the operations include providing a location indicator on the Internet to enable finding a gym capable of carrying out the translating.

55. The apparatus of claim 16, wherein the exercise routine on the portable memory device includes an instruction providing control over speed of the different type of exercise machine.

56. The apparatus of claim 16, wherein the operations include setting a filter of at least one of web subject matter or content in said profile.

57. The apparatus of claim 16, wherein the operations include controlling permission for another to form a group of users.

58. The apparatus of claim 16, wherein the operations include accepting, with said second computer system, a gym registration application communicated from the first computer system.

59. The apparatus of claim 15, wherein the operations include accepting, with said second computer system, a gym registration application communicated from a computer of the user.

60. The apparatus of claim 15, wherein the operations include managing, with said second computer system, a gym membership.

61. An apparatus including:
a computer system programmed so as to carry out the operations of translating a private personalized exercise routine, stored in and retrieved from a portable memory device, to a different private personalized exercise routine for each different type of user-selected exercise machine such that an exercise machine of at least one said type is controlled with one said different private personalized exercise routine.

62. The apparatus of claim 61, wherein:
the personalized exercise routine is stored in the portable memory device with respect to a first user-selected type of exercise machine;
and the operations include translating the exercise routine to an other type of user-selected exercise machine to enable carrying out the personalized exercise routine on the other type of exercise machine.

63. The apparatus of claim 61, wherein said apparatus comprises a computer system, where the exercise routine is formed, and programmed so as to facilitate user-triggered downloading of the exercise routine to the portable memory device.

64. The apparatus of claim 63, further including a virtual private network that allows access to the computer system in downloading the exercise routine from the portable memory device.

65. The apparatus of any one of claim 1, 15, or 61, wherein the operation of translating is carried out within a home gym.

66. The apparatus of claim 61, wherein the operations include specifying parameters of the exercise routine including type of machine, duration of session, intensity level, and pattern of variation of the intensity level.

67. The apparatus of claim 62, wherein the different type of exercise machine comprises one of at least a treadmill, an elliptical trainer, a stationary bike, a stationary ski machine, a stationary rowing machine, or a resistance type machine.

68. The apparatus of claim 62, further including a user computer programmed so as to specify a location corresponding to the different type of exercise machine.

69. The apparatus of claim 61, wherein the operations include controlling access to said exercise machine, via a virtual private network of computer devices corresponding to exercise machines, by associating a user identification name and a password to each of said devices.

70. The apparatus of claim 62, wherein the operations include forming a client profile database containing a profile for each of a plurality of users.

71. The apparatus of claim 62, wherein the operations include facilitating access to a virtual private network in scheduling an exercise session in which the exercise routine is to be carried out, the scheduling being carried out through a web browser interface, and the scheduling including selecting a location, date, and time.

72. The apparatus of claim 71, wherein the operations include configuring web viewing through the web browser interface, including: configuring screens of the web browser, said web browser interface stored on the other exercise machine; and selecting types of content to be viewed while exercising.

73. The apparatus of claim 71, wherein the operations include facilitating initiation of the exercise routine by receiving identification to the different type of exercise machine, the identification including at least one of a name and password on a keypad, information from a smart card to a reader, or information from a magnetic strip to a card reader.

74. The apparatus of claim 61, wherein the operations include communication of an indicator of a gym capable of carrying out the translating.

75. The apparatus of claim 62, wherein the operations include facilitating accepting, with said computer system, a gym registration application from a user personal computer.

* * * * *